(12) United States Patent
Zweig

(10) Patent No.: US 7,758,744 B2
(45) Date of Patent: *Jul. 20, 2010

(54) DUAL GLUCOSE-TURBIDIMETRIC ANALYTICAL SENSORS

(76) Inventor: Stephen Eliot Zweig, 224 Vista de Sierra, Los Gatos, CA (US) 95030

( * ) Notice: Subject to any disclaimer, the term of this patent is extended or adjusted under 35 U.S.C. 154(b) by 1273 days.

This patent is subject to a terminal disclaimer.

(21) Appl. No.: 11/263,500

(22) Filed: Oct. 31, 2005

(65) Prior Publication Data

US 2006/0051738 A1 Mar. 9, 2006

Related U.S. Application Data

(63) Continuation-in-part of application No. 10/264,206, filed on Oct. 3, 2002, now Pat. No. 6,984,307.

(60) Provisional application No. 60/327,535, filed on Oct. 5, 2001.

(51) Int. Cl.
G01N 27/327 (2006.01)
G01N 21/00 (2006.01)

(52) U.S. Cl. .................. 205/792; 422/57; 422/56; 436/164

(58) Field of Classification Search .................. 204/403.01–403.15; 436/14, 95, 128, 164; 205/777.5, 792; 422/55–58, 82.05–82.09
See application file for complete search history.

(56) References Cited

U.S. PATENT DOCUMENTS

| | | | |
|---|---|---|---|
| 3,586,862 A | 6/1971 | Topol et al. | |
| 3,665,301 A | 5/1972 | Maltby | |
| 3,714,444 A | 1/1973 | Carr et al. | |
| 3,814,668 A | 6/1974 | Blake et al. | |
| 4,055,768 A | 10/1977 | Bromberg | |
| 4,147,514 A | 4/1979 | Magers et al. | |
| 4,211,530 A | 7/1980 | Goverde et al. | |
| 4,225,410 A | 9/1980 | Pace | |
| 4,397,956 A | 8/1983 | Magio | |
| 4,545,382 A | 10/1985 | Higgins et al. | |
| 4,548,907 A | 10/1985 | Seitz et al. | |
| 4,682,895 A | 7/1987 | Costello et al. | |
| 4,841,157 A | 6/1989 | Downing, Jr. | |
| 4,910,402 A | 3/1990 | McMillan | |
| 5,049,487 A | 9/1991 | Phillips et al. | |
| 5,110,724 A | 5/1992 | Hewett et al. | |
| 5,114,350 A | 5/1992 | Hewett | |

(Continued)

FOREIGN PATENT DOCUMENTS

EP 1 113 263 A2 12/2000

(Continued)

OTHER PUBLICATIONS

JPO abstract of Ogura et al. JP 59-116545 A, patent published on Jul. 5, 1984.*

*Primary Examiner*—Alex Noguerola

(57) ABSTRACT

Diagnostic dry reagent tests capable of reacting with a single drop of whole blood and reporting both glucose and light-scattering analytes, such as chylomicrons, are taught. Such dry reagent tests may employ electrochemical detection methodologies, optical detection methodologies, or both methodologies. These tests alert diabetics to excessive levels of postprandial lipemia caused by meals with excessive amounts of fat, and thus can help reduce the risk of cardiovascular complications in diabetic patients.

20 Claims, 10 Drawing Sheets

U.S. PATENT DOCUMENTS

| | | |
|---|---|---|
| 5,126,275 A | 6/1992 | Hatch et al. |
| 5,139,685 A | 8/1992 | de Castro et al. |
| 5,171,688 A | 12/1992 | Hewett et al. |
| 5,344,754 A | 9/1994 | Zweig |
| 5,350,992 A | 9/1994 | Colter |
| 5,555,920 A * | 9/1996 | Godolphin et al. .......... 141/329 |
| 5,597,532 A | 1/1997 | Connolly |
| 5,628,890 A | 5/1997 | Carter et al. |
| 5,695,949 A | 12/1997 | Galen et al. |
| 5,708,247 A | 1/1998 | McAleer et al. |
| 5,734,468 A * | 3/1998 | McNeal ..................... 356/319 |
| 5,843,692 A | 12/1998 | Phillips et al. |
| 5,940,148 A | 8/1999 | Joseph et al. |
| 5,951,836 A | 9/1999 | McAleer et al. |
| 5,968,836 A | 10/1999 | Matzinger et al. |
| 6,027,692 A | 2/2000 | Galen et al. |
| 6,090,251 A | 7/2000 | Sundberg et al. |
| 6,143,164 A | 11/2000 | Heller et al. |
| 6,231,920 B1 | 5/2001 | Guadalupe et al. |
| 6,277,641 B1 | 8/2001 | Yager |
| 6,388,750 B1 * | 5/2002 | Liu et al. .................... 356/436 |
| 6,984,307 B2 * | 1/2006 | Zweig ..................... 205/777.5 |

FOREIGN PATENT DOCUMENTS

| | | | |
|---|---|---|---|
| JP | 59-116545 A | * | 7/1984 |
| WO | WO 99/58709 | | 11/1999 |

* cited by examiner

DUAL GLUCOSE-TURBIDIMETRIC ANALYTICAL SENSORS

This application is a Continuation in Part of application Ser. No. 10/264,206, "Dual glucose-hydroxybutyrate analytical sensors" filed Oct. 3, 2002 now U.S. Pat. No. 6,984,307, which also claimed priority benefit of provisional patent application 60/327,535 "Dual glucose-hydroxybutyrate analytical sensors", filed Oct. 5, 2001.

BACKGROUND OF THE INVENTION

1. Field of the Invention

The field of the invention is improved dry reagents for instrumented whole blood tests useful for diabetics.

2. Description of the Related Art

Blood glucose monitoring has revolutionized the treatment of diabetes. Large-scale clinical trials have demonstrated that frequent blood glucose monitoring can aid in the prevention of many of the long-term complications of diabetes, such as diabetic retinopathy, circulatory disorders, and death. After nearly twenty years of development, blood glucose monitoring has now become a several billion dollar a year business.

As the blood glucose-monitoring field has advanced, the various blood glucose monitors have become more and more generic. All possess good accuracy, ease of use, and speed. As a result, the various manufacturers of blood glucose monitors have focused major efforts on gaining minor technical advantages to make minor improvements in their respective market shares. Such improvements may include minor improvements in speed, blood sample size, ease of sample application, cost, etc. All, however, produce test strips that measure only blood glucose.

Although blood glucose is the most important biochemical parameter to measure in diabetes, it is not the only parameter of medical interest. Other parameters of medical relevance include glycosylated hemoglobin, used to measure long-term blood glucose control, ketone levels, used to indicate if the patient is at risk for diabetic ketoacidosis, and lipids such as cholesterol, triglycerides, lipoproteins, and chylomicrons, used to indicate the patient's relative risk of cardiovascular disease.

In this document, ketoacidosis and elevated triglycerides will be used as the main examples of other biochemical parameters that are medically relevant to the treatment of diabetes, however it should be understood that the methods discussed here are general purpose, and may be used for a wide variety of different analytes.

Diabetic ketoacidosis is a major complication of diabetes. Such conditions occur during times of extreme insulin deficiency. Here the diabetic's tissues are unable to process glucose, and as a result, initiate the biochemical processes that result in the formation of ketones and excess blood glucose. During periods of insulin starvation, body cells are unable to metabolize glucose as an energy source and instead metabolize fat as an energy source. Ketone bodies, made up of acectoacetate, acetone, and beta-hydroxybutyrate (also called D-3-hydoxybutyrate) are produced from this fat metabolism process, and these build up in the blood. Excessive levels of ketone bodies in turn can alter the pH balance of the blood to a more acidic state, as well as other undesirable complications, eventually leading to confusion, coma, and death. In the early stages of fat metabolism, the ketone bodies contain relatively large amounts of acectoacetate and acetone. However in more profound ketoacidosis, the ketone bodies contain primarily beta-hydroxybutyrate.

Each year, about 12 out of every 1000 diabetics are hospitalized for Ketoacidosis, and 2% of those hospitalized die from it. It is the commonest cause of death for diabetic children.

Early detection is the best way to prevent diabetic ketoacidosis. If detected in time, rehydration and low-dose insulin therapy can be used to treat ketoacidosis. Thus means to ensure that the onset of ketoacidosis is promptly detected are of extreme utility to diabetics.

Although ketoacidosis is a major problem, the biggest complication of diabetes is cardiovascular disease. Two out of three diabetics ultimately die from heart disease and stroke (caused by cardiovascular disease), and many others suffer from other cardiovascular disease complications such as diabetic retinopathy. Much of this cardiovascular disease in turn is caused by the build-up of fatty deposits (lipid rich plaque) in blood vessels and arteries.

Diabetics, and in particular type 2 diabetics, often have an abnormally large increase in the amount of triglycerides, lipids, and lipoproteins circulating in the blood after meals. This increase is particularly severe for type 2 diabetics who have just eaten meals with a high fat content. This post-meal lipoprotein increase is often referred to as "postprandial lipemia" In postprandial lipemia, a large number of triglyceride-rich chylomicrons, low-density lipoproteins (LDL), very low-density lipoproteins (VLDL) and other lipoproteins are released from the small intestine. These triglyceride-rich chylomicrons and other lipoproteins scatter light, and often cause the plasma and serum from postprandial subjects to have so much optical turbidity that this turbidity interferes with the optical determination of other analytes. As a result, for many clinical analytes, it is a routine clinical practice to require patients to fast for at least twelve hours before providing blood samples.

Recent studies have shown that this postprandial lipemia can do more harm than just generate turbid plasma. The LDL and chylomicron lipoprotein particles tend to build up on the walls of arteries, leading to atherosclerosis (fat deposits on artery walls) and subsequent increased risk of coronary artery disease, stroke, and other cardiovascular disorders.

Fortunately the choice between a high-fat diet that causes substantial postprandial lipemia, and a low-fat diet that avoids high postprandial lipemia, is a relatively easy choice to implement—substitute low-fat foods for high-fat foods. If type 2 diabetics, who are at a particularly high risk for atherosclerosis and other cardiovascular complications caused by postprandial lipemia, and who are accustomed to routinely testing postprandial blood glucose levels, also had a simple way of determining their relative level of postprandial lipemia at the same time, they would be constantly reinforced to chose low-fat diets, and thus could substantially reduce their risk of cardiovascular disease.

Returning to the ketoacidosis example, means to measure ketone levels are known in the art. These include visually read test strips for acetone or acectoacetate in the urine, as well as whole blood tests for beta-hydroxybutyrate. Diabetics are trained that whenever their glucose levels are high, they should follow up by immediately running a separate ketone test.

Examples of urine ketone dry reagent tests include Ketostix, Keto-Diastix (Beyer) or Chemstrip K (Roche). Such urinary tests generally use non-enzymatic detection methods (such as nitroprusside based chemistries) that are primarily sensitive to acectoacetate, slightly sensitive to acetone, and not at all sensitive to beta-hydroxybutyrate. One drawback of tests that measure only urinary acectoacetate or acetone is that such tests can miss or underreport extreme levels of ketoacidosis. In mild ketosis, the body produces acectoacetate, acetone and beta-hydroxybutyrate in relatively proportionate amounts, and thus urinary tests for acectoacetate and acetone will detect mild ketosis. However in extreme ketoacidosis, the body produces mostly beta-hydroxybutyrate and relatively small amounts of acectoacetate and acetone. Thus non-enzymatic nitroprusside based acectoacetate and acetone sensitive tests may become insensitive to extreme ketoacidosis right when they are needed the most.

Simple dry reagent whole blood tests for beta-hydroxybutyrate, the most clinically relevant indicator of ketoacidosis, are known in the art. Presently, such dry reagent tests use a disposable reagent that performs only the beta-hydroxybutyrate test. Often this disposable beta-hydroxybutyrate reagent is read in a meter that is capable of reading a number of different types of single test reagents. For example, GDS diagnostics, Elkhart Ind., sells the "Stat-Site™" meter, which can read separate calorimetric dry reagent tests for either whole blood glucose or ketones (beta-hydroxybutyrate). This technology is taught in U.S. Pat. No. 5,139,685. Polymer Technology Systems of Indianapolis Ind. sells the Bioscanner™ meter that can also read separate calorimetric dry reagent tests for either whole blood glucose or ketones. Similarly, MediSense sells the "Precision Xtra™" meter that can read separate electrochemical dry reagent tests for either glucose or beta-hydroxybutyrate.

Other one-meter multiple-reagents systems are in commercial use. The LXN Corporation sells the "Duet™" and "In Charge System™" meters that are capable of reading either a calorimetric glucose dry reagent test, or alternatively a colorimetric glycated protein (fructosamine) dry reagent test. These are discussed in more detail in U.S. Pat. Nos. 5,695,949 and 6,027,692.

Although diabetics are accustomed to testing their blood glucose several times a day, they may often forget to run a ketone test, since such tests require extra reagents and effort. Indeed, in an effort to correct for this normal human lapse, some glucose meters, such as the LifeScan "ultra" blood glucose system, will attempt to remind users to run ketone tests by an extra "Ketones?" meter prompt. However, clearly many diabetics will ignore this reminder.

Returning to the lipemia example, methods to measure postprandial lipemia are also known in the art. These tests include standard enzymatic tests for triglycerides, lipoprotein precipitation tests using chemical agents that selectively precipitate lipoproteins from plasma, and immunoprecipitation tests for specific lipoproteins (using specific anti-lipoprotein antibodies). Studies have also shown that there is a good correlation between the amount (level, concentration) of plasma or serum chylomicrons and the turbidity (light scattering) of the plasma or serum. Tazuma et. al. ("A quantitative assessment of serum chylomicron by light scattering intensity: Application to the intestinal fat absorption test", Journal of Gastroenterology and Hepatology, Volume 12(11), November 1997, pp 713-718) utilized this correlation to devise a clinical test for serum chylomicrons based on light scattering nephelometric, (turbidimetric) methods. Tazuma et. al. found that a linear relationship existed between serum light scattering (using serum diluted 1:10 into 0.9% saline) and triglyceride concentration. Specifically, in Tazuma's system, this relationship was shown by equation 1 below:

$$y=0.33[x]+14.969x \qquad \text{Equation 1}$$

Here "y" is the serum chylomicron triglyceride concentration (level) in mg/dl, and "x" is the relative extent of plasma light scattering on Tazuma's Nippon Shoji Micronephelometer MN-202, used for this experiment.

Although Tazuma's work shows that it is possible to use light scattering measurements to determine triglyceride levels in diluted serum, this is an unusual approach that has not previously been used for whole blood dry reagent tests. More typically, whole blood triglyceride dry reagent tests are based upon enzymatic reactions that produce a colored reaction product and are measured by a calorimetric instrument. Examples of this type of test include the Polymer Technology Systems (Indianapolis, Ind.) "Cardiocheck" system, and the Polymer Technology Systems "Lipid Panel" test strips. The "Lipid Panel" test strips measure total cholesterol, HDL (high density lipoprotein), and triglycerides using plasma obtained from whole blood by filtering the blood through a spreading layer, a blood separation layer, and a fractionation layer. The resulting purified plasma is then read in three separate enzymatic reaction zones, each zone containing a different enzymatic chemistry that generates a colorimetric reaction.

The Cholestech LDX analyzer (Cholestech corporation, Hayward, Calif.), exemplified by U.S. Pat. Nos. 5,110,724; 5,114,350 and 5,171,688 is another dry reagent triglycerides test that also measures total cholesterol, HDL, and triglycerides by a similar process in which whole blood is first fractionated into plasma, and then read in three separate enzymatically based calorimetric reaction pads. Due to the need to separate whole blood into plasma prior to contact with the various enzymatic reaction zones, both systems require relatively large amounts of blood and both systems are relatively slow The PTS Lipid panel test requires 40 ul of blood and requires two minutes to perform a test. The Cholestech LDX system requires approximately 60 ul of blood and requires about five minutes to perform a test. As a result, neither approach would be competitive in the blood glucose market, where sample sizes are invariably less than 20 ul, and test times are often only a few seconds are less.

Ideally, what is best from a medical perspective is a blood glucose test that automatically (without any extra user thought, process, or intervention) also reports blood beta-hydroxybutyrate levels, or blood lipid (triglyceride or chylomicron) levels, or other important second analyte levels, using the same drop of blood used to perform the standard and habitual glucose test. Indeed such a combined test would save many lives by facilitating the early detection of ketoacidosis, prevention of atherosclerosis, or other complication of diabetes. Additionally, such combined tests would be of strong commercial interest as well, since if everything else were equal, a combined glucose/beta-hydroxybutyrate test, glucose/triglycerides test, glucose/lipoprotein test, glucose/chylomicron test, or glucose/relevant-second-analyte test would be strongly preferred by diabetics over the glucose-only tests presently used.

However no such single-blood-drop-activated, combined blood-glucose/blood-beta-hydroxybutyrate dry reagent or combined glucose/lipoprotein reagent has previously been proposed, invented, or commercialized.

By contrast, combined glucose-ketone test strips have been available for urine testing for many years. Given the competitive nature of the blood glucose-monitoring field, why does this discrepancy exist between the long-term commercialization of combined urine glucose-ketone dry reagent test strips, and the complete lack of any prior art in combined high speed, low blood sample, whole blood glucose/beta-hydroxybutyrate or blood glucose-second analyte dry reagent tests?

The difference is almost certainly due to the radically different nature of the two different sample types. Urine is available in large (100+ milliliter [ml]) quantities. It is nearly transparent. Thus a combined glucose-ketone dry regent test may be made by simply putting a calorimetric glucose dry reagent test pad onto solid support a certain distance away from a colorimetric ketone dry regent test pad. Because large amounts of sample are present, the distance between the two test pads can be so great as to minimize any "cross talk" due to reaction intermediate or colorimetric dye indicator diffusion between the two pads.

It is often the case in nearly every area of technology that devices optimized for a single purpose outperform devices optimized for multiple purposes. Blood glucose testing has been a mature field for nearly twenty years, and blood glucose meters and reagents have evolved to a highly advanced state. Patients and physicians are unlikely to accept a dual glucose-beta-hydroxybutyrate or glucose-lipemia reagent as being a genuine improvement unless, at a minimum, the glucose portion of the reagent performs at a level that is competitive with stand-alone blood glucose tests. If the combined reagent requires no extra user effort, the blood glucose portion is competitive, and the extra cost for the secondary function is minor, then the user will benefit and the combined reagent will likely be a medical and commercial success.

In this context, the commercial success of combined urine-ketone test strips can be understood. These devices function with the same urine sample and require no additional user effort. The urine glucose part of a combined urinary glucose-ketone test strip performs as well as stand-alone urine glucose test strip.

By contrast, combined whole blood glucose-beta-hydroxybutyrate or other relevant glucose-second analyte dry reagents must overcome some formidable technical challenges. Whereas urine samples typically have a volume of 100 ml (milliliters), blood samples, typically derived from a fingerstick, are more typically have a volume around 1-10 ul (microliters), or more generally from about 0-20 ul. This is nearly five orders of magnitude less in size. Whereas urine is nearly transparent and relatively free of optical and electrochemical interfering substances, blood is intensely colored and contains nearly 50% hemoglobin and other strong optical and electrochemical interfering substances.

In order to meet the requirement for no additional user effort, a whole blood combined glucose-ketone/beta-hydroxybutyrate or other relevant glucose-second analyte test must place both the glucose sensing means and the ketone/beta-hydroxybutyrate (or other second analyte sensing means) close enough together as to both be activated with the same small (1-10 ul, or 0-20 ul) drop of whole blood. Further, the test must be designed to minimize "cross talk" between such closely spaced sensing means.

PRIOR ART

Visually read beta-hydroxybutyrate sensors and ketone sensors.

U.S. Pat. No. 4,147,514 teaches a urine test strip for detecting urinary acetone and acetoacetic acid by means of an improved nitroprusside reaction. This urinary ketone test strip patent, in conjunction with U.S. Pat. No. 3,814,668 for a urinary glucose test strip, forms the basis for the popular Keto-Diastix® Reagent strips for urinalysis, produced by Bayer Corporation, Elkhart Ind.

U.S. Pat. No. 4,397,956 teaches a whole-blood modification of the combined urine glucose-non-enzymatic ketone test strip. In this modification, a separate glucose reagent pad and separate ketone pad are mounted on the same support. Both pads are covered with a blood separation coating. Two drops of blood, one for each separate reagent pad, are applied to the device. The user manually times the reaction by allowing the blood to soak in for one minute, and then manually wipes or washes off the excess blood from the outer layer of the pad.

As taught, the device of U.S. Pat. No. 4,397,956 measures whole blood acetoacetate using the sodium nitroprusside reaction, rather than the preferred enzymatic beta-hydroxybutyrate specific reaction. Thus the test reagent of U.S. Pat. No. 4,397,956 would be expected to suffer from the previously mentioned beta-hydroxybutyrate insensitivity clinical deficiencies of this type of reaction chemistry. This clinical deficiency, on top of other test deficiencies such as the requirement for multiple blood sample application steps, and extensive user intervention (timing, washing) teaches against the need for a competitive and automated dual glucose/beta-hydroxybutyrate whole blood test.

Prior art for single analyte glucose electrochemical sensors can be found a variety of patents, including many assigned to Genetics International, Medisense, E. Heller, & Company, Therasense, Selfcare, Boehringer Mannheim, and others. These include U.S. Pat. Nos. 4,545,382; 4,711,245; 4,758,323; 5,262,035; 5,262,305; 5,264,105; 5,286,362; 5,312,590; 5,320,725; 5,509,410; 5,628,890; 5,682,884; 5,708,247; 5,727,548; 5,820,551; 5,951,836; 6,134,461 and 6,143,164;

Prior art for single analyte hydroxybutyrate electrochemical sensors was published by Batchelor, et. al, "Ampherometric assay for the ketone body 3-hydroxybutyrate" Analytica Chimica Acta 221 (1989), 289-294.

U.S. Pat. No. 4,225,410 discloses an integrated array of electrochemical sensors where each sensor is a complete self-contained electrically isolated electrochemical cell, mounted on a solid support that contains a plurality of such cells. As is the case for previous art covering multiple colorimetric reagent pads on a single solid phase support, placing multiple electrically isolated electrochemical cells on a single solid phase support is also unsuitable for small rapid, low cost, analysis of 1-10 ul volume whole blood samples. Due to the surface tension characteristics of blood, separation of a single 1-10 ul droplet of whole blood into multiple electrically isolated droplets must overcome surface tension effects, and thus is energetically unfeasible without the intervention of energy added by some extra mechanisms. Although such mechanisms are known in the art (e.g. U.S. Pat. No. 6,090,251, etc.), the extreme manufacturing cost sensitivity of practical blood glucose tests should be recognized. Any commercially practical dual-purpose glucose-beta-hydroxybutyrate or other relevant second analyte electrochemical sensor must be price competitive with mass marketed single purpose glucose sensors, which can typically be produced at costs of about 10-20 cents per sensor. This brutal economic constraint on manufacturing costs eliminates all but the simplest combined designs from consideration. At the present state-of-the art, it appears unlikely that means will be found to mass produce, for a total cost of 10 to 20 cents per unit, a fully functional combined purpose electrode-containing-reagent, that also contains extra mechanisms to reliably and almost instantly separate a microliter sized drop of blood into two or more electrically isolated droplets.

WO 99/58709 discloses dry reagent test devices with two electrochemical sensors, but fails to teach mixed electrochemical/optical devices or pure optical devices. No commercial product based on WO 99/58709 has been announced to date.

Prior art for electrically triggered optical test reagents includes U.S. Pat. Nos. 5,344,754 and 5,554,531.

Prior art for fiber optical biochemical sensors includes U.S. Pat. No. 4,682,895, which teaches fiber optical probes with sharp, 180-degree bends at the sensor tip. Other prior art includes U.S. Pat. No. 4,548,907, which teaches bifurcated optical probes for use with pH dependent fluorophores, and U.S. Pat. No. 4,910,402 which teaches a dual fiber optic sensor for drop-sized samples.

Prior art for turbidity sensors includes U.S. Pat. Nos. 3,586,862, 3,665,301, 3,714,444, 4,055,768, 4,211,530, 4,841,157, 4,910,402, 5,350,992 and 5,940,148.

SUMMARY OF THE INVENTION

The two major detection methods employed in modern dry reagent blood glucose tests are calorimetric (best exemplified by the LifeScan "One-Touch" and "SureStep" systems), and electrochemical (best exemplified by the Medisense "Precision" family of systems). All work with extremely small sample sizes, typically under 10 ul, and all are "automatic" in the sense that after the addition of a single drop of blood, all further analysis and data reporting is done automatically by the meter. These systems set the standard for performance that a successful combined glucose/beta-hydroxybutyrate; a combined glucose/chylomicrons or glucose/triglycerides, or other combined glucose/other-analyte reagent must match or exceed.

In this disclosure, reagents, systems and methods to add additional whole-blood beta-hydroxybutyrate detection and reporting means, additional chylomicron or triglyceride detection and reporting means, or other additional analyte detection and reporting means to novel and state-of-the-art blood glucose reagents are disclosed. Such systems and methods disclosed herein are designed to enable the combined test to have performance characteristics similar to modern dedicated single-purpose blood glucose reagents.

According to this invention, the main principle that applies throughout is that both sensors in the combined reagent device should be held so close together that both can be simultaneously rehydrated (or hydrated) and activated using a single, unseparated, whole blood drop. Because the two sensors are so close together, however, the system must also be designed to minimize "cross-talk" between the two different neighboring sensors.

Enzymatic detection schemes: To briefly review, glucose, beta-hydroxybutyrate, and many other relevant second analytes can be detected using a variety of different enzymatic schemes.

Glucose reacts with the enzyme glucose oxidase. In an electrochemical system, the electrons will then transfer to an electron transfer mediator molecule, such as ferrocine, and then enter the reagent's electrode. In an optical system, glucose oxidase will produce hydrogen peroxide. This in turn will react with a second enzyme, peroxidase, and an indicator dye molecule, such as a benzidine dye.

Alternatively, Glucose may react with a dehydrogenase enzyme, such as hexokinase/glucose-6-phosphate dehydrogenase. This will convert NAD to NADH. In an electrochemical test, the NADH in turn will undergo electron exchange with an electron transfer mediator molecule, such as 4-methyl-o-quinone. This in turn transfers electrons to the reagent's electrode. In an optical system, the NADH will in turn react with the enzyme diaphorase and an optical indicator molecule such as a tetrazolium dye like INT (2-(4-iodophenyl)-3-(4-nitrophenyl)-5-phenyl tetrazolium chloride).

Similarly, beta-hydroxybutyrate reacts with the enzyme beta-hydroxybutyrate dehydrogenase (E.C. 1.1.1.30). This will then convert NAD to NADH. In an electrochemical test, the NADH in turn will undergo electron exchange with an electron transfer mediator molecule, such as 4-methyl-o-quinone. This in turn transfers electrons to the reagent's electrode. In an optical system, the NADH will in turn react with the enzyme diaphorase and an optical indicator molecule such as a tetrazolium dye like INT (2-(4-iodophenyl)-3-(4-nitrophenyl)-5-phenyl tetrazolium chloride).

Turbidity detection schemes: As discussed by Tazuma et. al. ("A quantitative assessment of serum chylomicron by light scattering intensity: Application to the intestinal fat absorption test", Journal of Gastroenterology and Hepatology, Volume 12(11), November 1997, pp 713-718), and by Thorp et al (Thorp J M, Horsfall G B, Stone M C. A new red-sensitive micronephelometer. Med. Biol. Eng. Comput. 1967; 5: 51-6); turbidity measurements obtained by light scattering from small plasma or serum samples (micronephelometric methods) correlate well with chylomicron triglyceride levels obtained from more standard clinical assays.

A more detailed review of the various enzymatic methods may be found in: "Introduction to Bioanalytical Sensors" by A. Cunningham, published by John Wiley & Sons, 1998, the contents of which are incorporated herein by reference. A more detailed review of various turbidity (nephelometric) methods may be found in U.S. Pat. No. 5,940,178.

Techniques to correct for cross talk effects for two neighboring electrochemical tests were previously discussed in parent application Ser. No. 10/264,206, paragraphs 42-47, the contents of which are incorporated herein by reference.

Whole blood turbidity measurements pose challenges that have not been completely addressed by prior art. The pioneering work of Tazuma and Thorp, previously discussed, was performed with plasma or serum samples. Plasma and sera require that whole blood be centrifuged, subjected to membrane filtration, or subjected to a clotting process, and thus this type of sample is not suitable for incorporating into extremely rapid, extremely small volume, modern commercial blood glucose tests. Any attempt to measure the turbidity caused by chylomicrons and other lipoproteins in whole blood samples must contend with the very high interfering level of light absorption and light scattering caused by the large concentration of red cells. Red cell hemoglobin intensely absorbs visible light, making long optical pathways, required to generate an optical scattering signal, infeasible. Red cells also scatter light. As a result, optical interference caused by red cells tends to dominate the smaller amount of light scattering (turbidity) caused by chylomicrons, which is why previous workers chose to remove red cells and perform their light scattering studies with red-cell-free plasma or serum. To detect chylomicrons in whole blood using light scattering techniques, the analytical system must be designed to compensate for this very large red-cell optical background signal.

A number of techniques can be done to reduce the magnitude of the interfering red-cell optical signal to a manageable level. A first important step is to utilize the fact that red-cell hemoglobin has very low absorbance in the far-red and near infrared spectral region (Zijlstra, et. al. Clin. Chem. 37/9, 1633-1638, 1991), which enables much longer optical paths at these wavelengths (approximately 650 to 1400+ nm, where nm is the standard abbreviation for nanometers). A second important step is to utilize the fact that since red cells are much bigger than chylomicrons, red cells will tend to scatter light at different angles, and this difference in scattering efficiency as a function of angle can be used to separate the chylomicron and lipoprotein light-scattering signal from the background red-cell scattering signal.

The present invention utilizes these two facts: 1) longer optical paths through whole blood are possible at far-red and near infrared wavelengths, and 2) particles of different size scatter light at different angles; to construct extremely simple dual whole-blood glucose/lipoprotein test strips.

The optical equations used to calculate light scattering are well understood. One equation that is often used for light scattering calculations of this sort is Mie theory which describes the light scattering of particles of this approximate size (Johnsen and Widder, "*The Physical Basis of Transparency in Biological Tissue: Ultrastructure and the Minimization of Light Scattering*" J. Theor. Biol. (1999) 199, 181-198, and Ruf and Gould "*Size distributions of chylomicrons from human lymph from dynamic light scattering measurements*" Eur. Biophys J. (1998) 28: 1-11).

Mie theory calculating programs, such as "Scatlab" (Bazhan V., Scatlab 1.2 software, www.scatlab.com) allow researchers to calculate the amount of scattering, as a function of scattering angle, which is caused by various particle types under various conditions. Here the relevant parameters are the wavelengths of light (here near-infrared wavelengths of approximately 700 and 1000 nm can be used), average chylomicron diameter (approximately 0.1 microns, with a range between 0.05 and 0.3 microns), chylomicron index of refraction (about 1.46), average red cell diameter (approximately 5 microns, with a range between about 2 to 8 microns), average red cell index of refraction (about 1.4), and the index of refraction of the surrounding plasma media (about 1.34). Using these parameters, the Scatlab Mie calculator generates the following table of normalized scattering intensity at various angles, wavelengths, and particle types:

while giving relatively little additional "real estate" for other sensors, does provide enough room for optical backscattering detectors. In this configuration, both the light source and the light scattering detector (which may be as small as a light emitting optical fiber and a light receiving optical fiber) can be mounted on the same support base. This support base can also be used to hold the test-strip sensor electrodes as well.

Table I also shows that side-scattering and low-angle scattering turbidity detectors are also quite useful for whole blood turbidity measurements. The side-scattering geometry has its own set of advantages which tends to compensate for the somewhat more complex side-scattering test-strip design. In particular, note that the 0° angle (no scattering) parameter, shown in Table I, contains important information that can be used to compensate for (normalize) differences in illumination beam intensity. Side scattering designs also allow the sharp fall-off in the narrow angle red blood cell (RBC) scattering signal to be measured (note the Table I results showing that by 20°, the RBC scattering signal is almost zero). Additionally, the fairly large difference in scattering efficiency between the small 0.1 and medium 0.2-micron chylomicron particles at 700 nm and 1000 nm (Table I shows that at 45°, there is about a 2× difference between the 700 and 1000 nm results for 0.2 micron sized particles) can also be detected by use of a side-scattering geometry. This additional information can be used to more accurately estimate the true chylomicron concentration (since chylomicrons vary in size), as well as to

TABLE I

Relative (normalized) scattering intensity versus particle size, angle, and wavelength.

| | 700 nm | | | 1000 nm | | |
|---|---|---|---|---|---|---|
| Scattering angle | Small C .1 micron | Medium C .2 micron | RBC 5 micron | Small C .1 micron | Medium C .2 micron | RBC 5 micron |
| 0° (no scattering) | 100% | 100% | 100% | 100% | 100% | 100% |
| 20° to 0° ratio | 89.54% | 72.62% | 0.03% | 92.54% | 83.34% | 0.08% |
| 30° to 0° ratio | 78.81% | 49.70% | 0.02% | 84.56% | 67.36% | 0.03% |
| 45° to 0° ratio | 59.87% | 21.69% | 0.01% | 69.52% | 42.44% | 0.02% |
| 90° to 0° ratio | 27.16% | 2.96% | 0.01% | 39.82% | 12.40% | 0.02% |
| 160° to 0° ratio | 22.03% | 3.17% | 0.01% | 59.24% | 2.27% | 0.02% |
| 180° to 0° ratio | 21.68% | 3.05% | 0.01% | 61.76% | 2.17% | 0.02% |

In Table I, the scattering caused by two populations of chylomicron particles (small 0.1 diameter particles and medium sized 0.2 micron diameter particles), and the scattering caused by a representative red blood cell (5 micron diameter) population is shown at 0° (no scattering), 20, 30, 45, 90, 160 and 180° angles from the incident light. These calculations are done at two near-infrared wavelengths (700 nm and 1000 nm), which are not absorbed by red cell hemoglobin, and thus penetrate for a substantial distance through whole blood.

The table I scattering data shows that back-scattering turbidity detectors, which measure scattering angles of approximately 180°, are particularly useful for this application. The chylomicron-sized particles generate a comparatively high degree of 180° backscattering, while red blood cells have almost no 180° backscattering. Thus the 180° backscattering signal is almost totally caused by chylomicrons, which simplifies data analysis. An additional advantage of the backscattering approach is that it is highly compatible with simple test strip designs. The small sample size and limited space available in a typical electrochemical blood-glucose test-strip, better correct for distortion caused by red blood cell interference and other optical interference.

Thus for each type of test methodology, electrochemical or optical, the multiple test device must be designed to promote rapid access of a small (typically 20 ul or less) sample of whole blood to two different test sensors, and also must be designed to minimize cross-talk between the different test sensors or between the analyte and the red cell background. To the extent that some cross-talk still persists, the meter that reads the reagent may be designed in a way to facilitate the collection of sufficient data, and have sufficient onboard computing means, to do further analysis and mathematical deconvolution in order to accurately separate the two different signals, and distinguish them from background interferences.

DETAILED DESCRIPTION OF THE INVENTION

Example 1

Combined "Sandwich" Electrochemical Glucose, B-Hydroxybutyrate Sensor with Glucose and Beta-Hydroxybutyrate Electrodes on a First Surface, and a Single Reference Electrode on a Second Surface The "sandwich" design has certain advantages from the user interface perspective. This design acts to "sip" a small drop of blood into an interior cavity formed by the various layers. This helps to partially protect the sample from the outside environment during the reaction.

Although in examples 1 and 2 given here, glucose oxidase type electrodes are illustrated, it should be understood that the principles taught herein would apply to glucose dehydrogenase type electrodes and electrodes for other enzymatically detected analytes.

Methods:

A detailed discussion of the methods to construct suitable NADH and Hydrogen peroxide specific electrodes, as well as glucose and hydroxybutyrate specific electrodes, was previously discussed in parent application Ser. No. 10/264,206, paragraphs 54-61, the contents of which are incorporated herein by reference.

Figure 1:
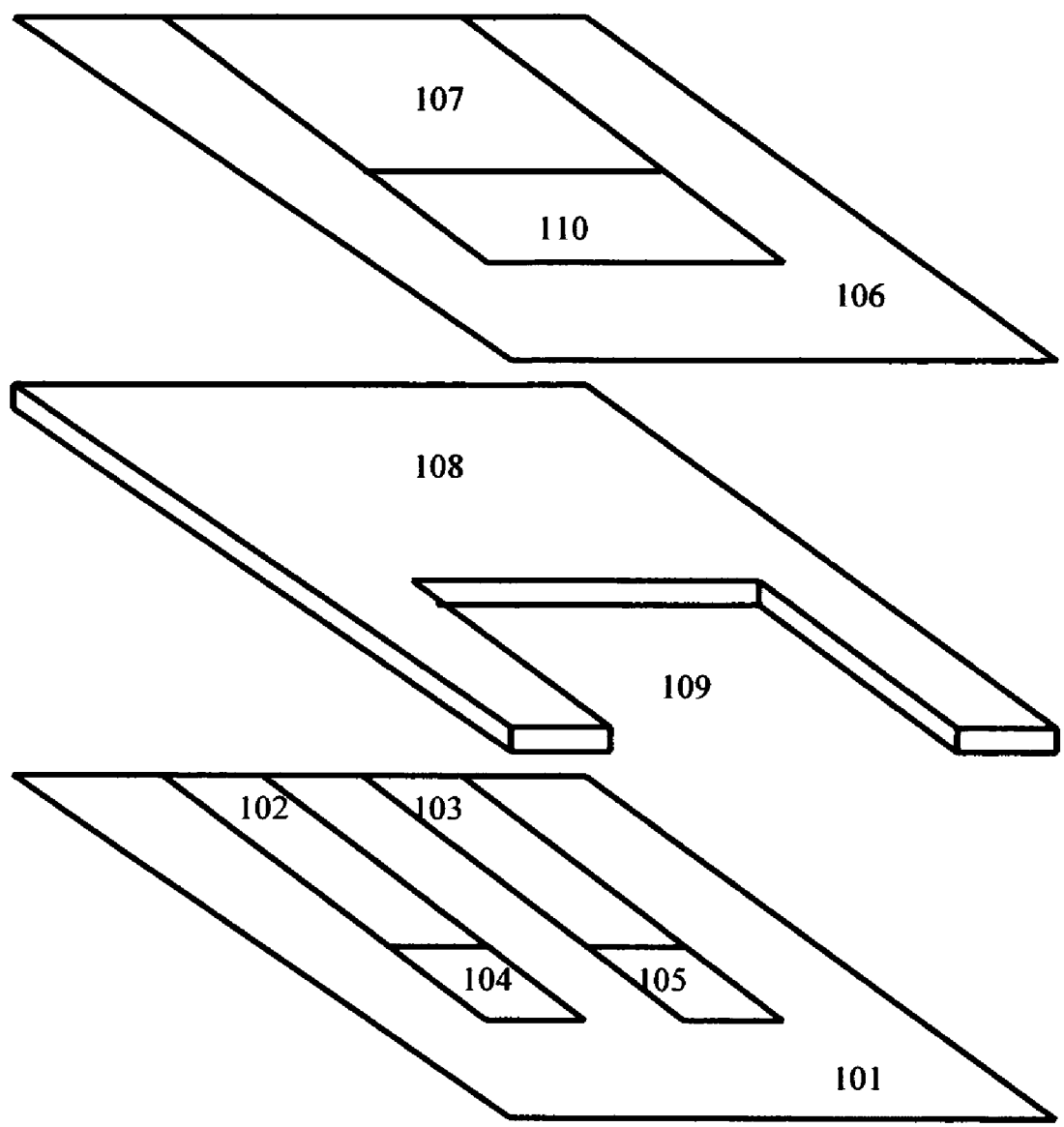
FIG. 1 shows a "sandwich" dry reagent electrochemical biosensor with glucose and beta-hydroxybutyrate electrodes on one surface, a chamber open on one end for receiving blood, and a reference electrode on a second surface.

A diagram of a "sandwich" type prototype sensor is shown in FIG. 1.

The prototype sensor may be produced by multiple screen-printing steps. Here the two working electrodes (102 and 103) are put on the same flat sheet of PVC (101) (or suitably prepared flat sheet of light-pipe material, if a secondary turbidity test is desired. Here "PVC" will be used to refer to any type of suitable flat support), and the reference electrode (107) printed on a second sheet of PVC (106), and then laminated on top of the fist PVC sheet with spacer (108) to form a sandwich structure with an opening to admit blood (109).

The PVC sheet (101) holding the glucose and beta-hydroxybutyrate working electrodes may be prepared as follows: In the first printing step, the traces (102, 103) connecting the electrode areas to the external electrical connection means may be printed. In the second step, the NADH electrode (104) can be printed. In the third step, the $H_2O_2$ electrode (105) is printed. In the fourth step, the NADH electrode (104) is overprinted with buffered saline solution containing 30 U/M1 D3-Hydroxybutyrate dehydrogenase, 10 mM NAD. In the fifth step, the $H_2O_2$ electrode (105) is overprinted with a buffered saline solution containing 10,000 U/ml of aqueous *Aspergillus Niger* glucose oxidase. Each working electrode is 1 mm wide, and the two electrodes are separated by a gap of 1 mm. After each printing step, the electrodes should be dried in a convection oven at 65° C. for 30 minutes and then stored in a cool, dry, environment until the next printing step.

The PVC sheet holding the reference electrode may be produced in two screen-printing steps. In the first printing step, the traces connecting the electrode areas to the external electrical connection means are printed (107). In the second step, the reference electrode silver-silver chloride electrode (110) is made by screen printing Gwent product C61003D7 onto 20 mil thick PVC substrate using 156 mesh polyester screen. The electrodes are then dried in a convection oven at 65° C. for 30 minutes and stored in a cool dry environment until used. The reference electrode may be 3 mm wide.

The two PVC layers should then be laminated together with an additional 10 mil (0.254 mm) thick spacer layer to result in a sandwich electrode with 3 mm×3 mm sized electrode surface area, and an internal volume of about 2.2 ul. Note that the electrodes on surfaces 106 and 101 all face the interior of the cavity.

A detailed discussion of electrical sensing methods used to read the electrochemical test strips was previously discussed in parent application Ser. No. 10/264,206, paragraphs 67-71, the contents of which are incorporated herein by reference.

Other electrode chemistries and production methods are also possible. As an example of one alternative, electrodes can be produced in general accordance with the sol-gel graphite composite technology as taught by U.S. Pat. No. 6,231, 920.

Methods to construct suitable graphite composite electrodes were previously discussed in parent application Ser. No. 10/264,206, paragraphs 73-78, the contents of which are incorporated herein by reference.

Coating electrodes with an inert hydrophilic, microporus layer: In order to help exclude as many interferents from the working area of the electrodes as possible, it is often advantageous to employ various microfiltration schemes to exclude red cells and other interferents. This may be done by a variety of means. The electrodes themselves may be designed to be microporous, as is taught by U.S. Pat. No. 6,231,920. Alternatively, or in combination, the electrode assembly may be covered with a microporous electrically inert material designed to admit sample while excluding as many interferents as possible. Such layers may be composed of previously synthesized filter materials, or built-up de-nouveaux on the test strip by means of self self-assembling chemical compositions, such as the mixed hydrophobic-hydrophilic particle techniques taught by U.S. Pat. Nos. 5,708,247 and 5,951,836.

Methods to construct suitable microporus layers were previously discussed in parent application Ser. No. 10/264,206, paragraphs 80-82, the contents of which are incorporated herein by reference.

As previously discussed, it is often advantageous to cap electrodes with such electrically inert microporus structures to reduce interference. Alternatively, such electrically inert microporous structures may be employed as "spacer" layers between stacked arrays of active electrodes, as is discussed in example 2.

Example 2

Multi-Layer Combined Glucose, Beta-Hydroxybutyrate Sensor

In an alternative embodiment, a porous spacer layer may be coated on top of the two sensor electrodes, and the reference electrode in turn coated on top of the spacer layer. Because the reference electrode is now elevated a significant distance above the primary support, an elevated stage with a secondary-conducting path may be added. Here a drop of blood is added directly to the primary support.

This "flat" reagent has its own unique set of advantages. Its more open design facilitates manufacturing. Additionally, some users may prefer applying sample to the more open reagent area.

Figure 2:
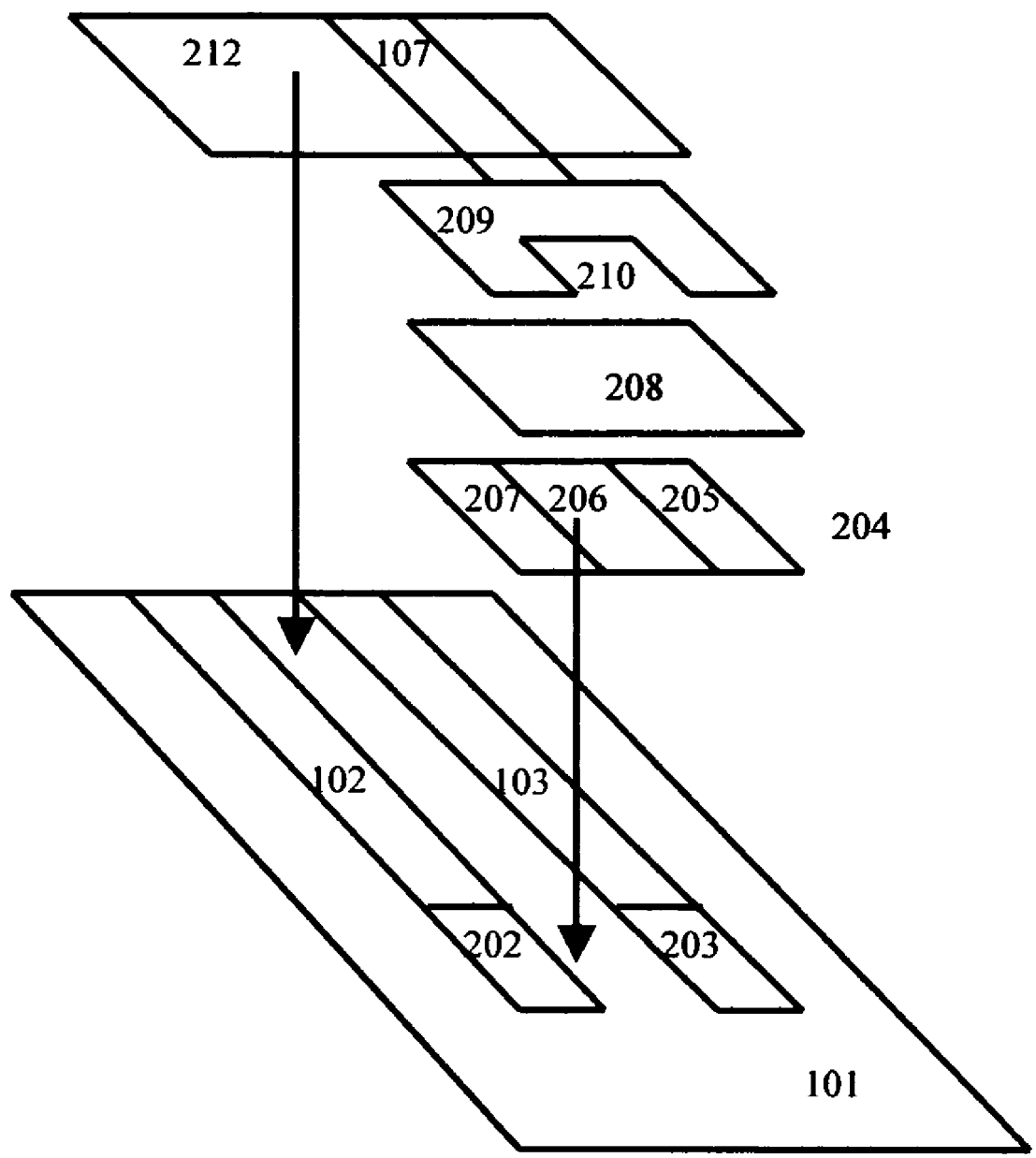
FIG. 2 shows a "flat" electrochemical dry reagent biosensor with glucose and beta-hydroxybutyrate electrodes on one surface, and a reference electrode located above the surface.

This scheme is shown in FIG. 2. In this scheme, conducting electrical paths (102, 103) are laid down on support (101) followed by the glucose and beta-hyroxybutyrate electrodes (202, 203). Usually this is done by a screen-printing process. In subsequent screen-printing processes, porous spacer layer (204) is printed to help fluid flow. Glucose and beta-hydroxybutyrate reagents (205, 207) are printed on top of the porous spacer layer and are absorbed into the layer. A second porous spacer layer (208) is then printed. An elevated stage (212) to carry the reference electrode signal to the meter may then be added, either by lamination or thick film printing. Finally, reference electrode (209) and reference electrode conductive paths (107) are printed. This reference electrode may contain one or more open regions (210) to allow the applied sample to flow to the lower layers. In some embodiments, it may be advantageous to apply a final porous layer on top of reference electrode (209) to stabilize the electrode stack, and reduce imprecision due to hematocrit effects or other interferents.

In operation, a drop of blood is placed on top of reference electrode (209). The blood flows through electrode gap (210) into porous spreading layer (208). The blood then flows into porous electrodes (207) and (205). Electrical signals from glucose and beta-hydroxybutyrate production (202, 203) are conducted to the meter through electrical paths (102, 103). The reference electrode signal is conducted to the meter though elevated electrical path (107) on an optional different surface (212) elevated above first surface (101).

Although electrochemical based glucose tests are rapidly becoming the preferred modality for this type of reagent, it is also possible to create simple, easy to use, one blood drop activated optical glucose+beta-hydroxybutyrate (or other relevant second analyte) reagents as well. This is shown in example 3.

Example 3

Optical Combined Glucose/Beta-Hydroxybutyrate (or Other Relevant Second Analyte) Test Strip In this example, a blood separating membrane, such as the membranes produced using the highly asymmetric membrane technology of the Filterite division of Pall corporation ("asymmetric polysulfone membranes", see U.S. Pat. Nos. 4,774,192 and 5,968,836) may be used to conduct the basic reaction. Typically filter membranes rated between 0.8 and 0.2 microns are preferred for this purpose. Asymmetric polysulfone membranes, used in this example, have a variable porosity structure with a large pore side on one side of the membrane, where sample is typically applied, and a small pore side, where the reaction results are typically observed.

Red cells in the blood sample applied to the large pore side migrate only partially into the membrane matrix, where they become trapped. By contrast, the plasma portion of the blood is free to move all the way to the small pore side. The membrane has sufficient optical opacity that if whole blood is applied to the large pore side of the membrane, only clear plasma is observed on the small pore side. Thus the color and reaction obscuring properties of the red cell hemoglobin are removed from the reaction. By embedding the appropriate reaction chemistry into the membrane, various types of chemical analytes can be observed, in particular, glucose and beta-hydroxybutyrate.

The small pore side of the membrane can be left open to the air. Alternatively, the small pore side may be covered with a transparent layer. Such transparent coverings may be desirable to improve reaction uniformity, resistance to environmental variables, and to reduce the chance of plasma from the sample contaminating the underlying meter. Such transparent membranes can reduce oxygen flow to the reaction however. Although this is not a problem for non-oxygen dependent enzymatic reactions, such as the beta-hydroxybutyrate reaction, it can be a problem if the commonly used glucose oxidase reaction for detecting glucose is used. Such glucose detection reactions are oxygen dependent, and thus might function sub optimally if the reaction matrix has a transparent layer that does not conduct oxygen well.

In this situation, use of the hexokinase glucose (glucose dehydrogenase) detection chemistry may be favored, since such reactions are not oxygen dependent. Additionally, such reactions use a number of the same reaction intermediates (NAD-NADH) and enzymatic reaction facilitators (diaphorase) etc., as the beta-hydroxybutyrate reaction. This may simplify test reagent construction, since the base membrane may be coated with reaction chemistry common to both enzymatic reactions, and the chemistry specific to each particular reaction may be then applied or streaked on in subsequent steps.

In order to work with a single 1-10 ul sized drop of blood, both the glucose and the second analyte (such as beta-hydroxybutyrate) reaction zones should be situated close to each other. As an example, membrane in the reaction zone may be coated with the glucose specific chemistry on one half, and the beta-hydroxybutyrate chemistry on the other half. The two half sides may be separated by a gap, or by a semi-permeable "speed bump" zone. Alternatively, the membrane may be intermittently sealed in a dotted line fashion between the two sides, so that cross-diffusion between sides is reduced, yet the two areas still remain in fluid communication.

Since beta-hydroxybutyrate or other second analyte detecting reagents will tend to be expensive, in an alternative configuration, it may be preferable to spot a smaller "dot" or "stripe" of the second analyte reagent onto a membrane otherwise nearly 100% saturated with the glucose reagent. In this case, the second analyte chemistry should be selected as to be resistant to the distortions caused by the large amount of neighboring glucose detection chemistry. This may be accomplished by a variety of means, such as incorporating a hydrogen peroxide absorbing or inactivating chemistry in the second analyte reagent. In this case, the user will either be expected to judge the color of the dot or stripe by eye, or alternatively the meter may contain means, such as a linear photodetector array, etc., to image the spot or stripe, and calculate and report a separate measurement.

In yet another alternative embodiment, the two regents may be applied to the surface of neighboring optical fibers or optically conductive pathways (such as an optical "light pipe"), one reagent per optical light-pipe. A holder that exposes both fibers to the same drop of blood may hold these optical light pipes together. In this case, the meter will contain means to independently interrogate the two optical light pipes, and report separate measurements.

In order to help visually distinguish this combined analyte test strip from the more commonly used single analyte test strip, it may be advantageous to include a tracking dye with either the glucose specific or second analyte specific second coating. A user could then use the colored stripe to help visually distinguish the combined test strip from the single analyte test strip.

In order that the tracking dye not interfere with subsequent colorimetric analysis of the reaction (either visual or photometric), it would be further advantageous if the dye rapidly undergo a transition from colored to uncolored (or alternate color) soon after sample application. Any dye that does not otherwise interfere with the reaction chemistry may be used here. As one example, the pH tracking dyes methyl red or phenol red may be applied to the surface of the membrane in a thin layer at pH that is mildly acidic relative to the rest of the reagent membrane. This thin layer is rapidly air dried immediately after application to keep the tracking dye distinct from the rest of the reagent in the membrane.

Under mildly acidic conditions, suitable pH tracking dyes absorb intensely around 520-550 nm and appear yellow. Upon application of sample, the dyes will mix with the more alkaline conditions in the applied sample and dried buffer from the rest of the membrane reagent, transition to a less acidic environment, and change their spectral properties. In particular, the dyes intense absorbance at 520-550 nm will stop (and thus the observed reflectance in the spectral region between 500-580 nm will increase), and instead the dyes will absorb at around 435 nm, and appear red. One advantage of this spectral response is that many indicator dyes useful for glucose and beta-hydroxybutyrate reactions have absorbance maximums that extend well into the 600 nm region, and thus there will be no additional cross-talk with the less acidic form of the pH indicator dyes. Many other dye reactions are possible and suitable, however.

A further advantage of such a tracking dye that undergoes a colored to clear transition upon hydration is that it can be used to help insure correct registration and tracking in an automated meter reader system. A frequent problem with such tests is that if a test strip reagent is not fully inserted (for example is only inserted so that half of the reaction zone is visible to the photo-optical reader), and then triggered by a optical reflectance drop (such as taught by U.S. Pat. Nos. 5,049,487; 5,843,692 and 6,268,162), then there is a significant possibility that the reaction would proceed with the meter reading only part of the colorimetric indicator. This could result in a potentially serious measurement error.

A meter designed to read a visually based combined functional glucose-second analyte test strip will normally have two photodetector systems, one designed to read the glucose portion, and the other designed to read the second analyte portion.

The asymmetric polysulfone membranes used in the examples here differ from the nylon membranes previously employed in the reflectance drop triggering methods of U.S. Pat. Nos. 5,049,487 and 5,843,692. Typically the color drop upon the placement of blood on an asymmetric polysuflone membrane is considerably less than the color drop upon the placement of blood on a nylon membrane. This is because the red-cell lytic nature of nylon membranes causes hemoglobin to rapidly transfer to the observation side of the nylon membrane. By contrast, non red cell lytic membranes, such as asymmetric polysuflone membranes, conduct relatively small amounts of hemoglobin to the observation side of the membrane. Thus use of reflectance drop techniques to detect sample application is relatively problematic when using reagents employing non-red cell lytic membranes are used.

By contrast, use of the color change of a tracking dye, induced by sample induced membrane hydration, has a number of advantages for test triggering purposes. Here, the test reagent is optimally designed so that the test strip must be fully inserted in order to bring the tracking dye portion of the membrane into full view. The meter can then be programmed to repeatedly interrogate the reflectance of the tracking dye portion of the membrane. Upon addition of sample, the tracking dye will then transition from a colored state to a non-colored state (or alternate color state), and the increase in reflectance at one or more wavelengths can then be used to trigger the start of the reaction. If the test strip is not fully inserted, or if the wrong type of test strip is used, the device will not trigger. This provides extra protection against user errors.

Modern blood glucose meters are extremely fast, and to be competitive, a dual-purpose glucose-second analyte reagent/meter system must also be as fast as possible. Here the reaction chemistry imposes some constraints, however. A sample with a high level of glucose or beta-hydroxybutyrate will typically take longer to complete than a reaction with a low level of these analytes. By necessity, an instrumented test that waits a fixed amount of time after reaction initiation in order to be sure to properly measure a sample containing a higher level of analytes will proceed with sub-optimal time efficiency with samples containing a lower level of analytes. In order to be as fast as possible, therefore, it is further advantageous to photometrically sample the reagent multiple times during the reaction, make real-time assessments as to if the reaction is heading to completion, and terminate the variable length test as soon as feasible.

Figure 3:
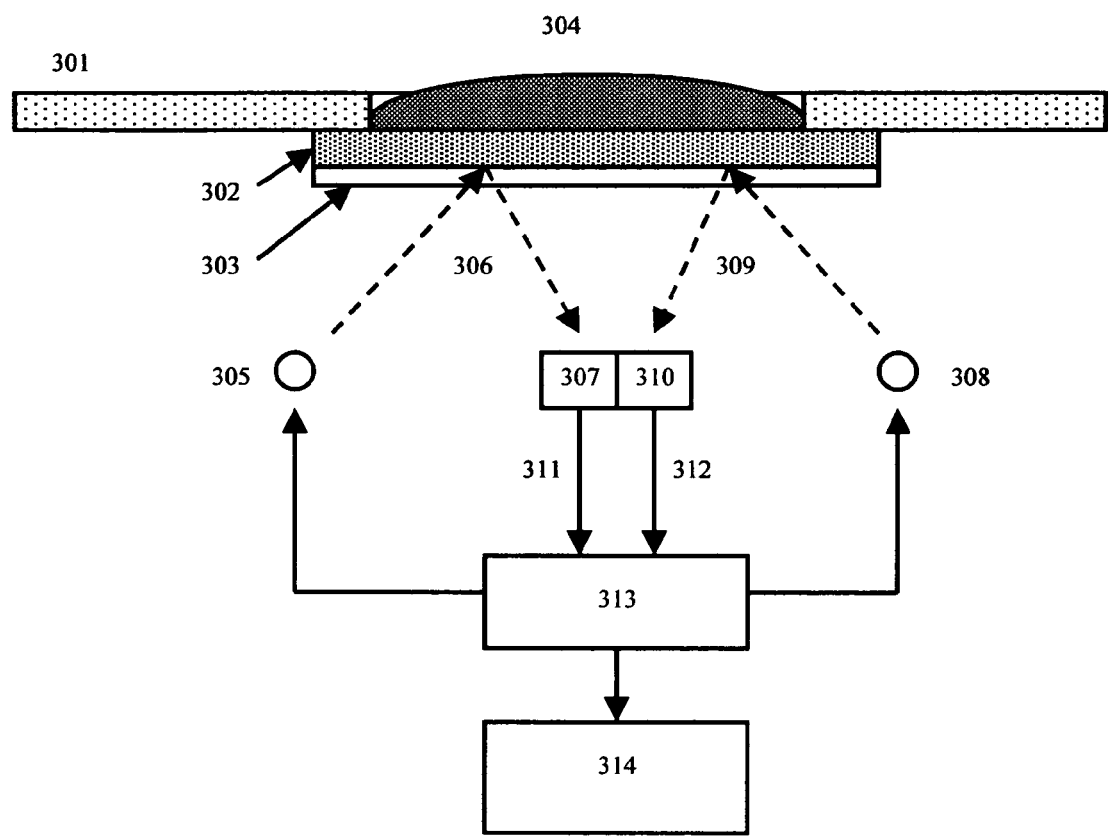
FIG. 3 shows a combined optical analyte dry reagent test strip/meter system. The test strip contains a single blood separating membrane, with regions striped with glucose detection reagents on one track, and beta-hydroxybutyrate detection reagents on the other track.
Figure 3:
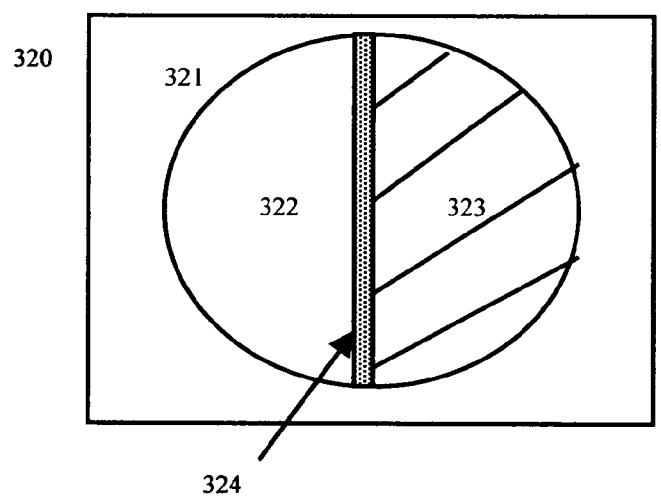

FIG. 3 shows an exemplary combined optical glucose, second analyte sensor. A plastic support (301) with a center aperture carries membrane (302), which may be covered by optional transparent layer (303). In this example, both the glucose and the exemplary beta-hydroxybutyrate reaction use dehydrogenase enzymes.

Label 320 shows a view from the top of plastic support (301) looking down on membrane (302) from above. Center aperture (321) can be seen. Membrane (302) has typically been first coated throughout with a reaction solution typically containing a buffer, reaction cofactors such as NAD and diaphorase enzyme, and typically one or more polymers and non-glucose sugars to stabilize the reaction components, and helps modulate fluid flow. Membrane (302) will also contain two tracks. These tracks are usually produced by a second overcoating step using a thin layer of overcoat reagent solution followed by rapid drying.

One track (322) will contain the complementary enzyme for one of the two test reactions, such as hexokinase glucose, an indicator dye, and other reaction cofactors. A second track (323) will contain the complementary enzyme for the other test reaction, such as beta-hydroxybutyrate dehydrogenase and other reaction cofactors. A second reagent indicator dye, (ideally with a different spectral response from the first indicator dye to minimize cross talk), will also be included. The second reagent track will usually be separated by gap (324) from the first reagent track.

Often, it may also be advantageous to include a moisture sensitive tracking dye (shown as the crosshatched area in (323)) that changes color from dark to light upon the addition of sample, into one or more of the two reagent tracks.

In operation, 1-10 ul (more generally 0-20 ul) of whole blood (304) is applied to the sample-receiving (open pore in the case of asymmetric polysulfone) surface of membrane (302). Red cells and plasma are separated and plasma flows through to the optical reading side, which may be covered by optional transparent membrane (303). The reaction zones (322) and (323) become hydrated with sample.

While this is going on, the underside of the test strip is being observed by a microprocessor controlled optical stage underneath the membrane (305-312). In operation, the optical stage periodically polls the state of tracking dye-coated membrane (323). This is done by a light source (308), controlled by microprocessor (313). This light illuminates the underside of the test strip (302, 303) and is detected by a microprocessor-controlled photodetector (310).

Typically light sources (305) and (308) will be provided by light emitting diodes (LEDs), and have defined spectral characteristics. In particular, light source (308) will optimally have spectral characteristics optimized to be sensitive to the color transition of the tracking dye, and also sensitive to the color transition of the indicator dye. If one LED does not have the required wavelength spectral properties for both purposes, two LEDs (or other light sources) with different spectral properties may be used in (308).

Upon sample addition, tracking dye (323) alters its spectral state and the increase in reflectance on at least one wavelength is detected by photodetector (310). This initiates test timing. Both reaction zone areas (322) and (323) are observed periodically by light source (305) and photodetector (307) (for zone (322)) and by light source (308) and photodetector (310) (for zone (323)). Note that depending upon the optical geometry, the same photodetector may be used for both (307) and (310).

The microprocessor (313) monitors the kinetics of both reactions. When it accumulates enough data points to either determine reaction rate, or extrapolate reaction endpoint levels, microprocessor (313) stops accumulating further data, calculates the final answer, and typically will display both answers on display (314).

In an alternative embodiment, the device of FIG. 3 can be configured to be a dual glucose-blood turbidity sensor. In this alternative embodiment, half of the membrane (portion 322) is omitted, and the transparent support 303 is present. As a result, the 322 portion of window 321 allows a direct view of the blood sample, while membrane 323 allows an analyte, such as glucose, to be determined by the enzymatic calorimetric techniques discussed previously. In this scheme, light-emitting diode 305 is configured to emit near-infrared light (i.e. light with a wavelength greater than about 650 nm), and photodiode 307 is configured as a backscattering turbidity detector. This backscattering signal can then be converted to a triglyceride concentration (using a conversion equation such as equation 1), chylomicron concentration, or other marker of relative lipemia levels.

Example 4

Combined Electrochemical—Optical Sensor

In this example, a hybrid detector element is formed containing one detection element based upon electrochemical technology, and a second detection element based upon optical technology.

Here, the electrochemical element may be a conventional electrochemical detector element, such the electrochemical glucose sensors discussed previously. The optical element may be a membrane based optical sensor, such as the optical membrane beta-hydroxybutyrate sensors discussed previously, or an alternate type of optical sensor.

One advantage of electrochemical sensors, however, is that the sensor element only needs to be connected to a meter by an electrical contact. As a result, electrochemical sensor-meter systems can be designed in which the electrochemical detector protrudes a significant distance away from the main body of the meter. This improves the user interface, because a drop of blood can be more easily applied to the protruding sensor. Additionally, it is often easier to insert or remove sensors if they stick out from the main meter body.

By contrast, membrane based optical sensors typically need to be held closely to the optical portion of a meter. This makes sample application more difficult, as applied blood thus has a higher chance of smearing onto non-sensing regions of the meter body, creating an undesired mess.

To avoid these ergonomic issues, it may often be advantageous to use an optical conductive pathway, such as a molded optical wave guide, optical fiber, "light-pipe" or the like to transmit the optical signal from the second optical sensor to a detection device. The optical wave-guide carries the optic signal along the same pathway used to conduct the electrical signals. Because the optical reagents need be applied only to the tip of the optical wave-guide probe, only extremely small amounts of reagent and blood are needed for the reaction. As a result, an optical sensor may be added to an electrochemical sensor with only minimal perturbation to the design of the electrochemical sensor.

Figure 4:
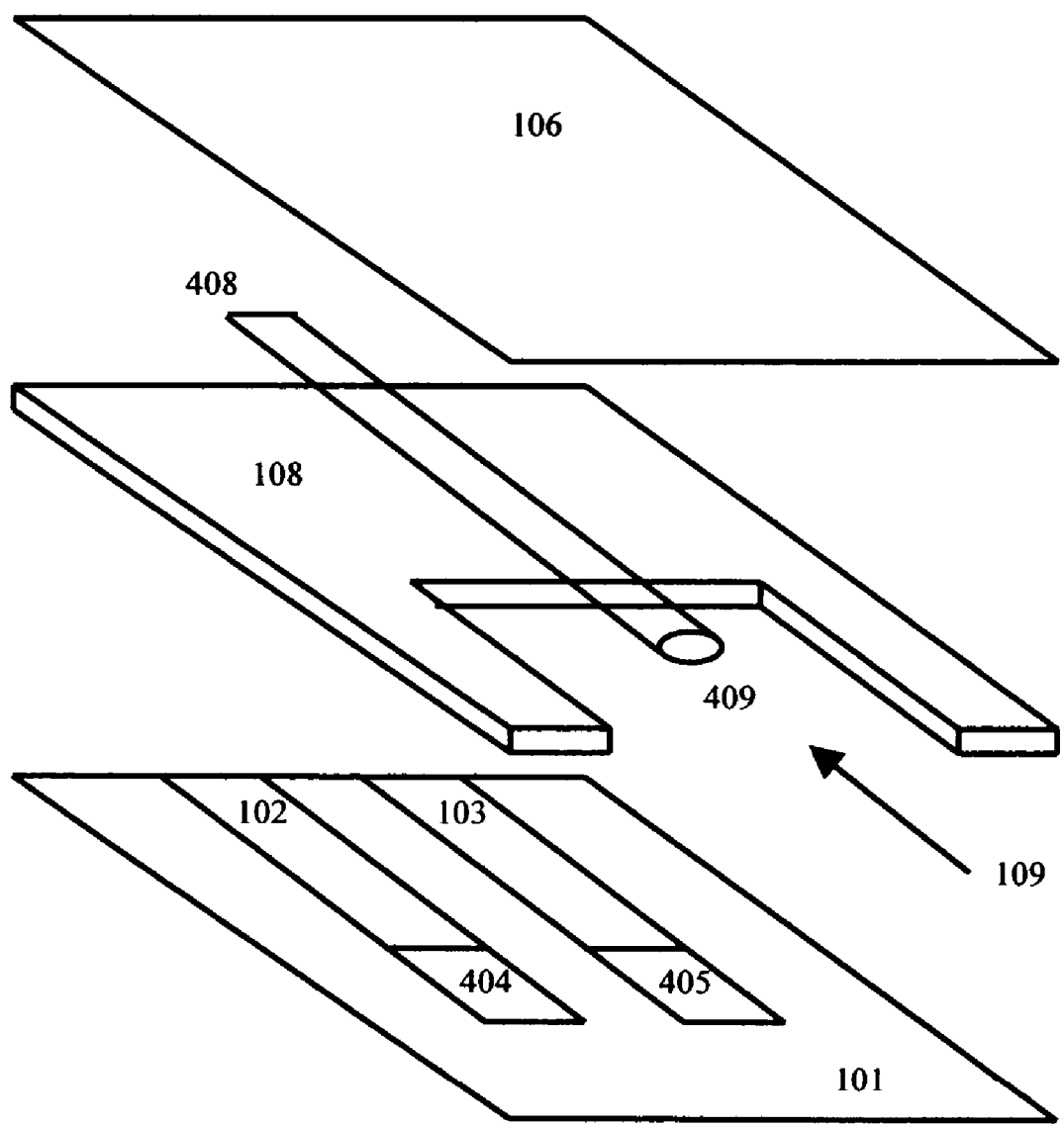
FIG. 4 shows a dual mode optical-electrochemical sensor. This test strip consists of an electrochemical glucose sensor, and a fiber optic sensor, mounted so that both sensors can read the same drop of blood.

A diagram showing this combined electrochemical optical sensor is shown in FIG. 4. Here, the support substrate (101) contains electrodes (102, 103) making contact with conventional glucose electrochemical reagents (404, 405). This, in turn, is separated by a spacer layer (108) from second support substrate (106). In practice, first support substrate (101), spacer (108), and second support substrate (106) are combined to form a single unit, containing a chamber (109), which is used to receive the blood sample.

The unit additionally contains at least one optical waveguide element (408) placed between support substrate (101) and (106). This optical wave-guide may be tipped with a colorimetric, fluorescent, or luminescent reagent (409), such that the analyte in the blood admitted to reaction chamber (109) produces a detectible optical signal, which is transmitted to an optical detection apparatus or meter by way of optical wave guide (408). Alternatively, when a turbidimetric or other measurement not requiring a separate reagent is used, the optical wave guide (or light pipe) need not be tipped with any reagent.

The configuration of optical wave-guide or light pipe (408) may be optimized for the specifics of the meter design and reaction chemistry. In some embodiments, it may be desirable to utilize an asymmetric design in which the meter side of the optical wave-guide is larger than the sample side of the optical wave-guide. This will facilitate optical coupling between the meter's optical excitation source and detector, and the wave-guide. At the same time, the sample side of the wave-guide can be kept extremely small, which minimizes the amounts of reagents and blood needed for the test.

Reagents, if needed, may be applied to the sensor end of the optical wave-guide with appropriate particulate or polymeric agents so as to create a relatively tough, but fluid permeable, cap on the tip of the wave-guide. Reaction chemistry indicator dyes and detection wavelengths may be chosen to give optimal signal-to-noise ratios with whole-blood samples. This favors the use of indicator dyes and detection wavelengths operating in the red and infrared end of the spectrum (greater than 650 nm), where interference from the hemoglobin present in whole blood is relatively minimal.

For colorimetric detection chemistries, it may often be advantageous to use multiple wavelength detection means employing both an indicator dye detection wavelength, and a reference wavelength where the indicator dye does not absorb as strongly. In this way, distortion of the calorimetric signal due to varying levels of hemoglobin or other interfereants in the sample may be minimized.

The configuration of the optical wave-guide may also be optimized for the problem at hand. As an example, in some situations, it may be advantageous to employ a dual chamber optical wave-guide with separate or partially separate optical conduits for the excitation signal and return signal. In other cases, a plurality of optical wave-guides may be advantageous.

For configurations employing reagents generating an optical signal, and single-fiber optical wave guides (fiber optics), use of fluorescent indicator dyes has certain advantages. The excitation wavelength, and the return fluorescent wavelength from the indicator dye, may travel through the same optical fiber with minimal confusion or cross-talk. Due to the extreme cost sensitivity of high volume mass-market glucose test strips, simple designs such as this are helpful. Simple reagent designs, which use minimal amounts of optical materials or reagents, have inherently lower production costs.

In the single fiber configuration, the reagent test-strip itself is kept extremely simple to reduce costs. Here, the single optical fiber is plugged into the optical unit of a meter, and any additional optical processing, beam splitting, and the like is performed by the meter's optical sensor unit. Ideally, to reduce costs to a minimum, the meter's optical sensor device is a miniaturized integrated optical chip, such as a MEMS optical chip.

In operation, sample is applied to reaction chamber (109). This sample interacts with the electrochemical sensor, producing a change in the electrical characteristics of the electrodes, such as an amperometric, potentiometric, conductometric, impedance, or other electrically detectible change, that signals the start of the test.

The meter will contain both electrical means to monitor the electrochemical reaction, and optical means to monitor the optical reaction. The meter monitors the reaction progress of the electrochemical reaction through electrical contact with electrodes (102, 103). The meter uses the same electrical signal used to trigger the start of the electrochemical reaction to begin monitoring the optical reaction through optical contact with optical wave guide (408).

Usually, but not always, the electrochemical reaction will proceed faster than the optical reaction. The meter may be programmed to immediately report the electrochemical reaction, and additionally may be programmed to either always display the optical reaction, or alternatively only display the optical reaction if the results of the electrochemical reaction suggest that the optical reaction results may be medically relevant.

As an example, the meter may be programmed to immediately report glucose, and not indicate that a second beta-hydroxybutyrate reaction is proceeding, unless the glucose results fall into a high range where ketoacidosis is a genuine possibility. However if the glucose level falls into a range where ketoacidosis is a potential concern, the meter may display an alternative message such as "Wait-checking ketones" while the ketone test automatically continues. In this way, the test may proceed with optimum speed most of the time, while still providing a valuable emergency ketoacidosis warning.

Alternatively, when a dual glucose/lipoprotein (triglycerides, chylomicrons) test is desired, and the lipoproteins are detected by light scattering (turbidimetric) methods that are also very fast, the meter may display the glucose measurement as a number and the turbidimetric chylomicron or lipoprotein light scattering measurement as a bar graph of varying height. The human factors advantage of this mixed numeric-graphic display is that the less critical chylomicron reading will not distract the user from the more immediately urgent numeric blood glucose reading. This mixed display still allows both results to be read at a glance, however. Many other display schemes, such as large and small numbers, different colors, etc. are also possible.

Note that although FIG. 4 shows a fiber optical wave guide operating in conjunction with an electrochemical sensor where both electrodes are on the same solid support, it should be obvious that these concepts will apply equally well to other electrode configurations as well. As an example, each electrode could be mounted on a different support surface, such as surfaces (101) and (106). Alternatively, electrode configurations as shown in FIG. 2 may be used.

Figure 5:
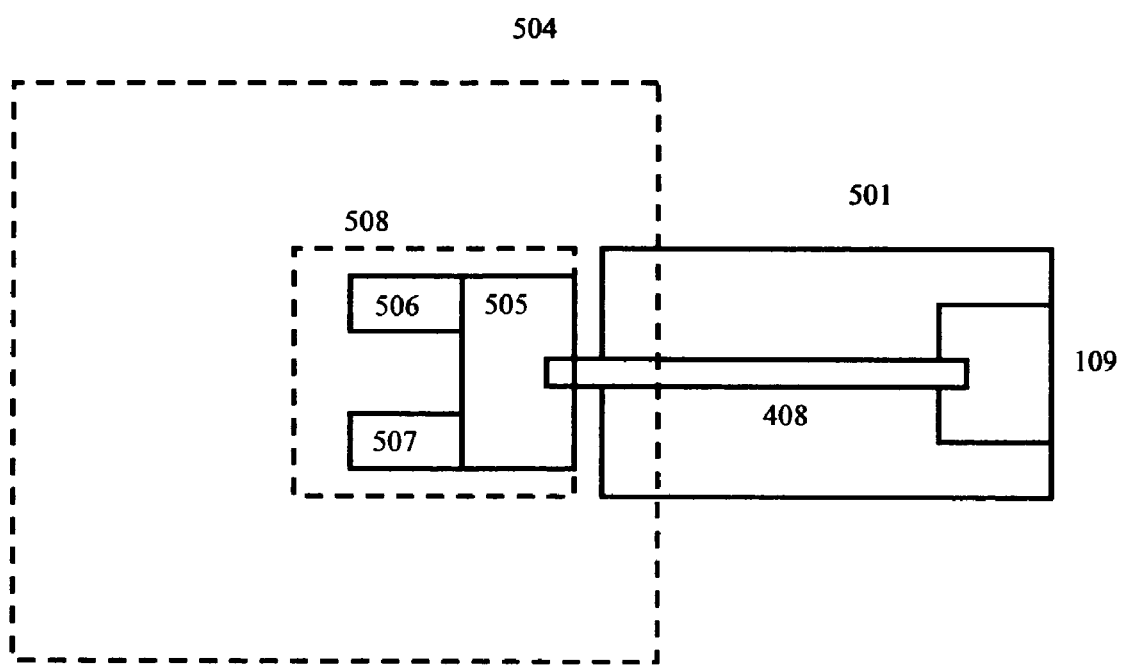
FIG. 5 shows a detail of the docking and optical interface between a dual mode optical-electrochemical sensor, and a meter. Here, the optical sensor consists of a single strand of optical fiber, capped with reagent.

FIG. 5 shows a close up of the interface between a test strip (501) containing an opening to admit a sample (109), a single fiber optic sensor (408); docking to meter (504). This test strip may additionally contain electrochemical sensor electrodes (not shown) that also make contact with meter (504).

In this scheme, optical fiber (408) docks with an optical adapter element (505), which further may split the optical signal between a wavelength emitter element (506) and a detector element (507). Ideally, to reduce manufacturing costs, two or more of these detector elements and or adapter unit (505) are integrated onto a single custom optical chip (508). The information from the optical detector, and the electrochemical detectors, is then processed by a microprocessor, converted to a clinically useful set of values, and communicated to the user.

Figure 6:
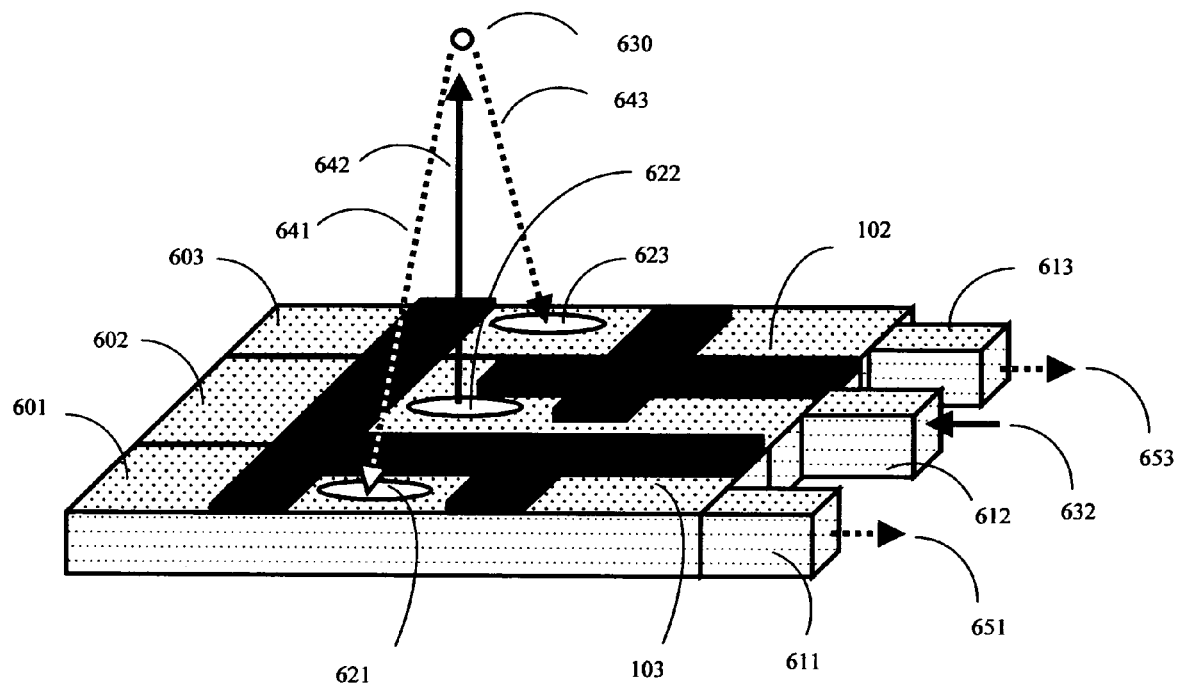
FIG. 6 shows a "flat" dual mode electrochemical blood glucose test strip and optical backscatter turbidity sensor, enabling simultaneous glucose and chylomicron determinations.

FIG. 6 shows a combination glucose-backscatter turbidity sensor based upon a flat electrode configuration. In FIG. 6, the support material consists of two or three (three are shown) optically separate optical wave-guides or light-pipes 601, 602, and 603 (typically constructed of a transparent material, such as thin transparent plastic, with dielectric properties compatible with the electrochemical sensing portion of the test. Alternatively fiber optic fibers can be mounted on an appropriate support material) laminated together to form a flat base. To minimize interference from outside light and also to minimize cross-talk between light pipes, unless otherwise stated, the sides of each light pipe will usually be covered with an opaque (non-light conducting) material. However if the test-strip is to be mounted directly onto a meter optics block that performs the light scattering measurement, the support material may be transparent (not covered with an opaque material), and the light scattering may be observed directly.

One end of each light pipe is configured with a transparent optical connector 611, 612, and 613 so as to enable each light pipe to interact with an outside light source or optical detector on a meter (not shown). Each light pipe also has at least one additional optical window 621, 622, and 623, typically formed by a gap in the opaque material covering the various respective light pipes. The three laminated light pipes 601, 602, 602 will typically form a continuous flat surface. The glucose sensing electrodes (for simplicity, only the conducing traces are drawn, and the actual electrode reagent pads are not shown) 102 and 103 will typically be formed on this flat surface. These electrodes are normally opaque, and in some configurations it may be desirable to lay out the electrodes in such a configuration as to optimize the openings in the opaque material surrounding the light pipe, consistent with the creation of optical windows 621, 622 and 623.

In use, a drop of blood (not shown) containing glucose, red cells, and light scattering lipoproteins is applied to the top surface of the sensor. Light from a meter optical source 632 enters the optical connector 612 on light pipe 602. This light is conducted through the light pipe to light pipe optical window 622. There the light beam 642 exits window 622 and will illuminate the lipoproteins 630. Backscattered light 641, 643 from lipoproteins 630 then enters light pipes 601 and 603 through optical windows 621 and 623. This backscattered light is then conducted back through transparent optical connectors 611 and 613, where re-emerges as backscattered light 651 and 653. This can then be analyzed by the photodetectors on the meter.

The meter will also have electrodes capable of interfacing with test-strip electrodes 102 and 103.

In addition to providing chylomicrons for the light scattering determination, the applied drop of blood also hydrates meter electrodes 102 and 103. This signals the meter to perform a standard electrochemical blood glucose determination. At about the same time, the meter sends pulses of near-infrared light 632 through optical interface 612. If there is a high level of lipoproteins present in the blood sample, the backscattered light signal 641 and 643 will be relatively high. This will be detected by meter photodetectors analyzing the light signal 651 and 653 reemerging from optical interfaces 611 and 613. This signal can then be analyzed by the meter's microprocessor, and the user presented with a dual glucose-light scattering derived measurement. This light scattering measurement may be transformed by the meter's microprocessor, using a conversion equation such as equation 1, to a clinically relevant triglycerides, chylomicron level, or other measure of relative lipemic risk to guide the user in subsequent corrective action as needed.

Incoming light 632 may be composed of one or several wavelengths of light. If one wavelength is used, this will typically be a wavelength of about 700 nm or greater so as o have minimal absorption by the hemoglobin present in the sample's red blood cells. In some cases, however, it may be advantageous to use multiple wavelengths, such as 700 nm and either a shorter wavelength (useful for determining the amount of scatter caused by red cells in the sample) or a longer wavelength (useful for determining the relative size of the light scattering particles), or both. To reduce interference from outside light, the incoming light 632 will typically be switched on and off at high frequency intervals, and the meter's photodetector and analysis circuitry and program designed to use the light-off scattering signal to compensate for any stray background light signals that may interfere with the light-on scattering measurements.

Note that the locations of windows 621 and 623 do not need to form equivalent angles with light emitting from excitation window 622. Rather, it may be desirable to arrange windows 621 and 623 so that one window is closer to excitation window 622, and thus measures backscattered light closer to 180°, and the other window is further away from excitation window 622, and thus measures backscattered light at alternate angles. The relative difference in intensity between the two signals can thus be used to estimate the relative size of the light scattering particles, and further discriminate between light scattered by the smaller lipoproteins and the light scattered by the larger red-cells.

Note that although FIG. 6 shows a three light-pipe configuration, in a more minimal implementation, only two light pipes (for example 601 and 602) will be needed to implement this type of sensor. These two light pipes could consist of two fiber optic fibers, one for excitation, and the other to collect the scattered light. In still other alternative configurations, the third light pipe may be configured to directly sample the light output from the excitation light pipe 602, thus providing an excitation reference signal to the meter, which can be useful in normalizing or otherwise adjusting the light-scattering data for variations in the efficiency in light excitation energy.

Figure 7:
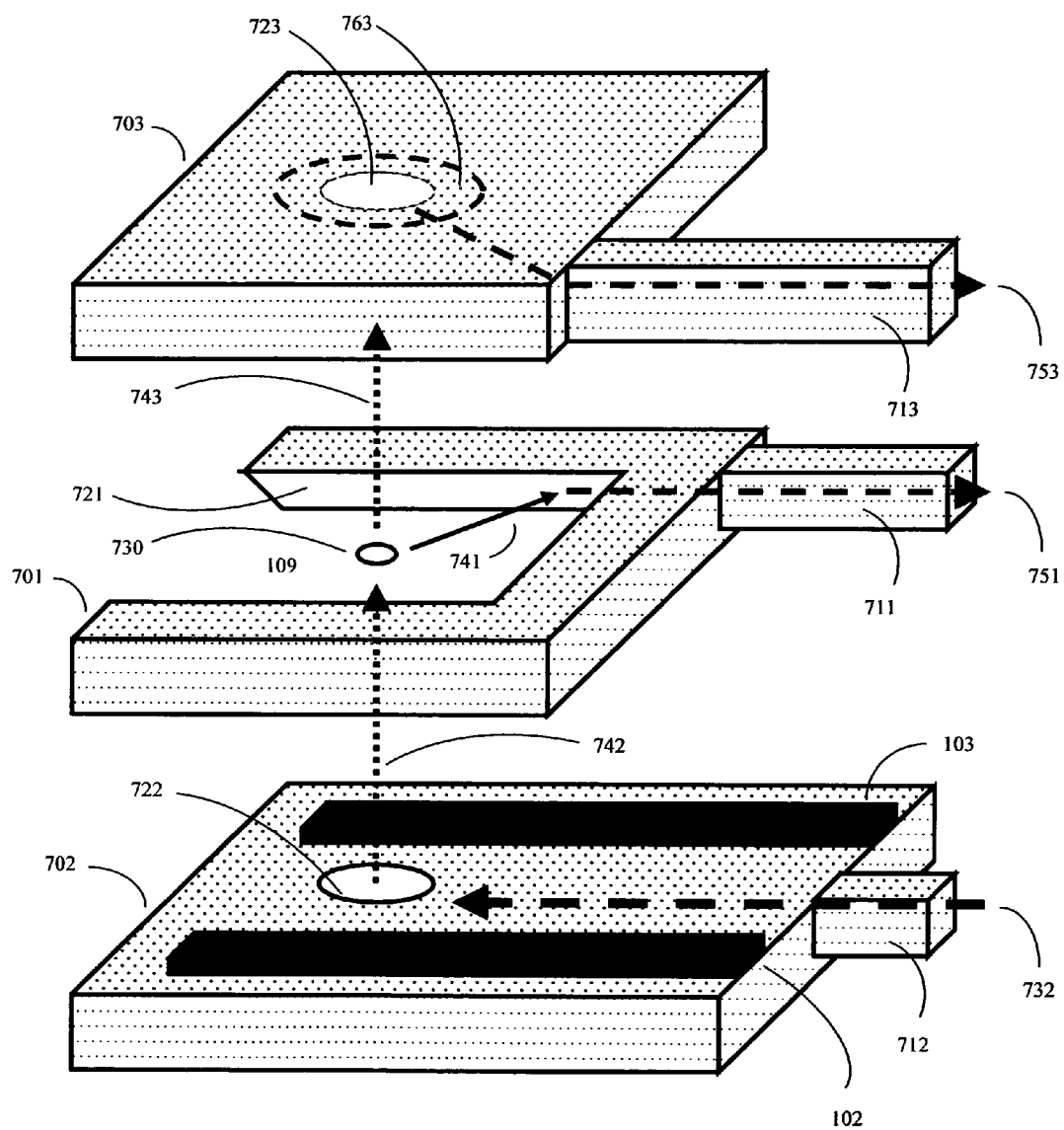
FIG. 7 shows an exploded view of a "sandwich" dual mode electrochemical blood glucose test strip and optical sidescatter turbidity sensor.

FIG. 7 shows an exploded diagram of a "sandwich-type" combination glucose-side scattering turbidity sensor, in which blood samples migrate into a sensor cavity by capillary action. In FIG. 7, the support material again consists of three optically separate optical waveguides or light-pipes 701, 702 and 703 (typically constructed of a transparent material, such as thin transparent plastic, with dielectric properties compatible with the test's electrochemical sensors, or alternatively fiber optic fibers mounted on an appropriate support material) and unless otherwise stated may be coated with an opaque (non-light conducting) material to minimize interference from outside light, and to minimize cross-talk between light pipes. One end of each light pipe is configured with a transparent optical connector 711, 712 and 713 so as to enable each light pipe to interact with an outside light source or optical detector (not shown). Each light pipe has either an additional optical window 722 or 723 or alternatively a central opening 109 through which light may traverse. The glucose sensing electrodes 102 and 103 will typically be formed on the top surface of light pipe 702. These electrodes are normally opaque, and in some configurations it may be desirable to lay out the electrodes in such a configuration as to optimize the openings in the opaque material surrounding the light pipe, consistent with the creation of optical window 722.

In use, a drop of blood (not shown) containing glucose, red cells, and light scattering lipoproteins (chylomicrons) is applied to opening 109 on the side of the sensor. Blood migrates into the central cavity 109 of the sensor by capillary action. Light from a meter optical source 732 enters the optical connector 712 on light pipe 702. This light is conducted through the light pipe to light pipe optical window 722. There the light beam 742 exits window 722 and will illuminate the lipoproteins 730. Side scattered light 741 from lipoproteins 730 then enters light pipe 701 through optical windows 721. This side-scattered light is then conducted back through transparent optical connector 711, where it re-emerges as sides scattered light 751. This can then be analyzed by the photodetectors on the meter and converted to a clinically relevant measurement by a conversion equation such as equation 1.

One advantage this side-scatter approach is that the non-scattered light 743 (or alternatively low-angle scattered light) can also be analyzed. This can then be used as a reference signal. If analysis of non-scattered light is desired, the placement of optical window 723 in light pipe 703 can be arranged directly over excitation light window 722. Non-scattered light 743 then enters light pipe 703, and is conducted to a photodetector on an outside meter (not shown) by way of optical connector 713, where it emerges as non-scattered light 753. Alternatively, if low-angle scattered light is desired, the optical window can be designed to be an annulus (ring) window 763 with the center part of the window 723 opaque to block non-scattered light, and the ring 763 transparent to allow low-angle scattered light to enter the device.

The meter will also have electrodes capable of interfacing with test-strip electrodes 102 and 103.

In use, a drop of blood is placed on the test strip. This rehydrates meter electrodes 102 and 103, and the meter performs a standard blood glucose determination. At the same time, the meter sends pulses of near-infrared light 732 through optical interface 712. If there is a high level of lipoproteins present in the blood sample, the side-scattered light signal 741 will be relatively high. This will be detected by meter photodetectors analyzing the light signal 751 and reemerging from optical interfaces 711. This signal can then be analyzed by the meter's microprocessor, and the user presented with a dual glucose-light scattering measurement. This light scattering measurement may be transformed by the meter's microprocessor to equivalent triglycerides, chylomicron level, or other measure of relative lipemic risk (such as postprandial lipemia analyte concentration) to guide the user in subsequent corrective action as needed.

Incoming light 732 may be composed of one or several wavelengths of light. If one wavelength is used, this will typically be a wavelength of about 700 nm or greater so as to have minimal absorption by the hemoglobin present in the sample's red blood cells. In some cases, however, it may be advantageous to use multiple wavelengths, such as 700 nm and either a shorter wavelength (useful for determining the amount of scatter caused by red cells in the sample) or a longer wavelength (useful for determining the relative size of the light scattering particles), or both. To reduce interference from outside light, the incoming light 732 will typically be switched on and off at high frequency intervals, and the meter's photodetector and analysis circuitry and program designed to use the light-off signal from the light scattering detection light-pipes to compensate for any stray background light signals that may interfere with the light-on scattering measurements. The difference in signal intensity between the side scattered light and the low-angle scattered light may also be used to determine the relative size of the light scattering particles.

Figure 8:
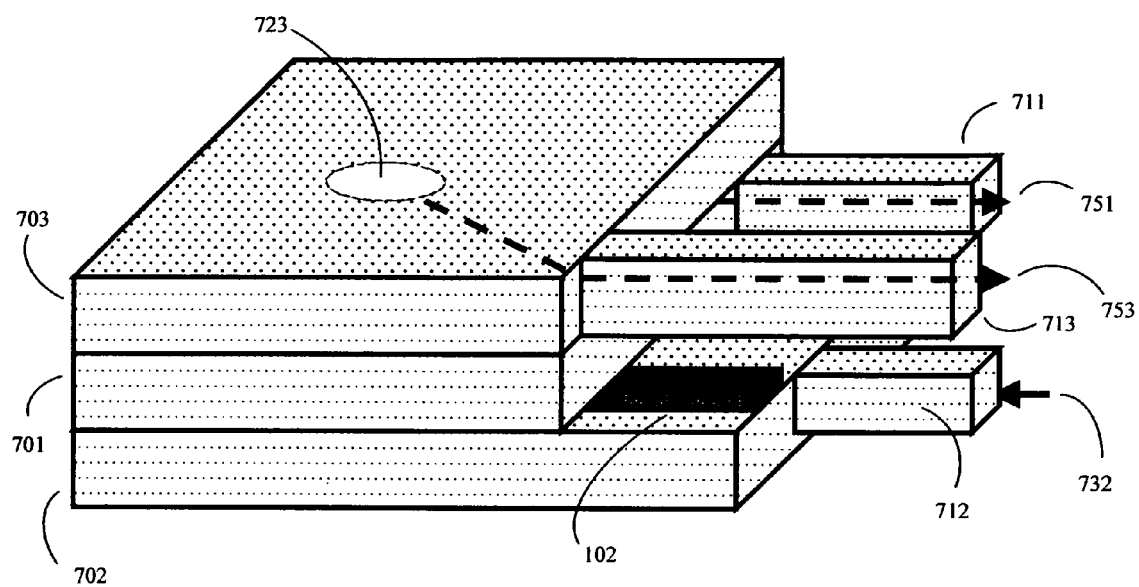
FIG. 8 shows a side view of the "sandwich" dual mode electrochemical blood glucose test strip and optical sidescatter turbidity sensor.

FIG. 8 shows a side view of the sandwich style dual glucose-side scattering turbidity sensor previously shown in exploded form in FIG. 7. In FIG. 8, the three light pipes 701, 702 and 703 are shown laminated together to form a single structure. The electrodes leading to the glucose sensors (here electrode 102 is shown, and 103 is hidden) are exposed to facilitate interface with socket on a meter capable of reading the glucose electrodes. The optical interfaces to the three light pipes, 711, 712 and 713 are also exposed and are also designed to slide into a meter socket, usually a combination electrochemical and optical socket on a meter designed to perform simultaneous electrochemical and optical determinations. This meter socket will provide excitation light 732 into the excitation light pipe 702 by way of optical interface 712. The meter socket will receive side-scattered light 751 from light pipe 701 by way of optical interface 751. The meter may also receive low-angle scattered light or a non-scattered light reference signal 753 from light pipe 703 by way of optical interface 713. This figure also shows a view of optical window 723, here used to return a non-scattered light reference signal 753.

Figure 9:
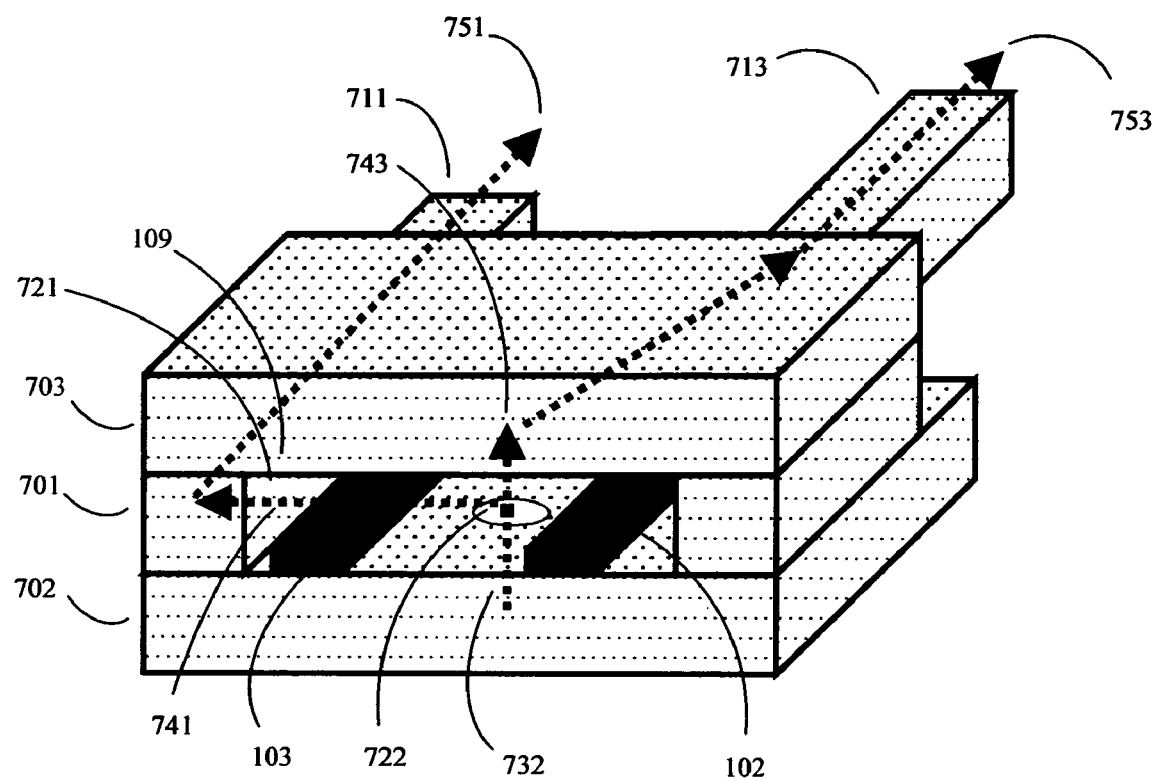
FIG. 9 shows a front view of the "sandwich" dual mode electrochemical blood glucose test strip and optical sidescatter turbidity sensor.

FIG. 9 shows a front view of the dual glucose-side scattering turbidity sensor previously shown in exploded form in FIG. 7, and in side view in FIG. 8. In FIG. 9, the three light pipes 701, 702, and 703 are again shown laminated together to form a single structure. The electrodes forming the blood glucose sensor 102 and 103 are also shown. The central cavity of the sensor, with the opening to admit blood, and the interior region where blood migrates by capillary action, is shown as 109.

As before, a small drop of blood is applied to the test strip and this blood fills the central cavity 109 by capillary action. The fluid in the blood sample (not shown) activates the blood glucose sensors, and electrodes 102, 103 electrically communicate the results. At the same time, lipoproteins (chylomicrons) in the blood sample (not shown) are illuminated by light 732 traveling through light pipe 702, and exiting light pipe 702 through optical window 722. Light side-scattered by the lipoproteins (741) enters light pipe 701 through optical window 721. This is transmitted by light-pipe 701 and exits the light pipe by optical interface 711 as signal 751, which is then read by a meter that connects to the optical interfaces and electrodes by a socket (not shown). Non-scattered light or low-angle scattered light 743 enters light pipe 703. This in turn is transmitted by light pipe 703 and exits the light pipe by optical interface 713 as signal 753. This is read by the same meter.

Alternate configurations are also possible. In an alternate embodiment of FIGS. 7-9, the lower support 702 is transparent, the upper support 703 is made up of a black, non-reflective material, and the turbidity is measured by an optical system shining near-infrared light through support 702, and measuring the backscattered turbidity through support 702, using a meter similar to FIG. 3 sections 305, 306, 307, 311, 313, and 314. At the same time, electrodes on the meter can make contact with the electrodes on the electrochemical test strip, again allowing simultaneous glucose and backscattering turbidity measurements to be performed.

Figure 10:
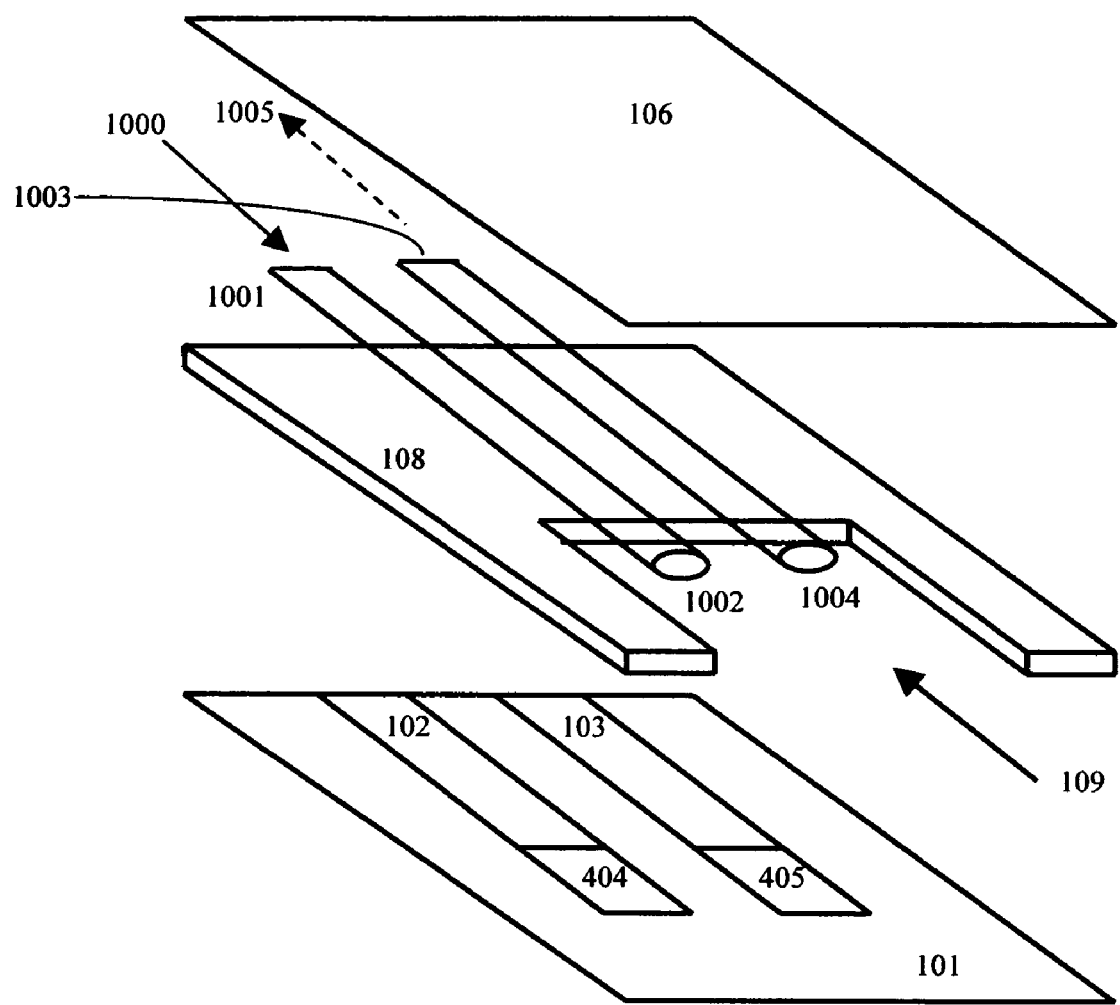
FIG. 10 shows a simple, two fiber-optic, dual mode electrochemical blood glucose test strip and optical backscatter turbidity sensor.

A particularly simple test strip configuration, somewhat favored due to the lower manufacturing cost, is shown in FIG. 10. FIG. 10 shows a "sandwich" type electrochemical blood glucose test strip, similar to that previously shown in FIG. 4, with two fiber-optic fibers 1001 and 1003 accessing the central cavity 109. Near infrared light 1000 from the external meter (not shown) enters central cavity 109 through fiber end 1002. In this configuration, optical fiber end 1002 is usually not tipped with any reagent. This light illuminates central cavity 109. When a drop of blood is applied, it enters into cavity 109 by capillary action, and an electrochemical blood glucose reaction is performed as previously described. At the same time, chylomicrons in the blood sample scatter the light emitted by optical fiber end 1002. The roughly 180° backscattered light enters optical fiber 1003 by optical fiber end 1004. This backscattered light 1005 exits optical fiber 1003, is then analyzed by the external meter's photodetector, and is typically converted by a program running on the external meter's microprocessor into a clinically useful result indicating the extent of lipemia in the blood sample, using an equation such as equation 1.

To test configuration 10, a simple experiment can be done using a 2 kilohertz pulsed 850 µm LED fiber optic light source (RIFOCS 252A, Rifocs corporation [now Tempo Research Corporation], Camarillo, Calif.), a fiber optic power meter (RIFOCS 575L), and a fiber optic jumper. The fiber optic jumper is broken in the middle, the two fiber optic strands exposed and placed 1 mm apart on a 10-mil thick plastic sheet in a backscattering configuration (both fibers parallel with each other and pointing in the same direction). The apparatus can be challenged with a drop of whole blood obtained from a patient after a 12 hour fast, and with a drop of whole blood obtained from a patient 3 hours after eating an extremely fatty meal. The light scattering signal from the patients can then be detected on the RIFOCS 575L power meter. Typically the light scattering signal obtained from the blood of a fasting patient, as detected by the RIFOCS power meter, will be much less than the light scattering signal obtained from a postprandial lipemic patient.

Still another alternate configuration utilizes evanescent light. It is well known that light traveling through optical fibers penetrates several hundred nanometers beyond the border of the fiber into the outside medium. If the surrounding medium, which in this application will normally be whole blood, does not absorb or scatter the evanescent light, then the light will continue to travel through the fiber with undiminished intensity. However if the surrounding medium contains a high enough density of light scattering particles that come within the several hundred nanometer evanescent zone surrounding the optical fiber, then the intensity of light will be diminished, and a higher amount of light will leak out into the surrounding medium. This scattered light may in turn be captured by a nearby light pipe, and returned to the external meter for subsequent photometric light scattering analysis.

What is claimed is:

1. A dry reagent diagnostic device for the simultaneous analysis of two or more different analytes in a single application of a single sample of whole blood with a volume under 20 ul,
    wherein the first analyte is determined by a first detection zone, and a second detection zone, physically separated from the first detection zone, determines the second analyte;
    a fluid bridge formed by the applied sample connects the two detection zones;
    said first detection zone and second detection zone having materials and geometry selected to allow simultaneous activation of both zones by a single unseparated whole blood drop;
    said detection zone materials and geometry being selected so as to return detectable analyte signals in the presence of whole blood;
    said detection zone materials and geometry being selected as to generate a detectable sample application signal upon initial contact with whole blood;
    said detectable sample application signal being capable of triggering an automated detection zone reader which is capable of performing subsequent test timing in an automated manner;
    and at least one of the detection zones produces a detectable change in an optical signal.

2. The device of claim 1, in which the analytes are selected from the group consisting of glucose, beta-hydroxybutyrate, cholesterol, triglycerides, lipoproteins, and chylomicrons.

3. The device of claim 1, in which one detection zone is an electrochemical reaction zone, and the reaction detected is an electrochemical reaction, and the device contains at least one electrode.

4. The device of claim 1, in which at least one of the detection zones produces a detectable signal by an enzymatic or immunochemical reaction.

5. The device of claim 1, in which said optical signal is selected from the group consisting of colorimetric, fluorescent, light-scattering, nephelometric, turbidimetric, or luminescent signals.

6. The device of claim 1, in which a chemical sample application signal detection means is incorporated into at least one of the detection zones, and in which the chemical sample application signal detection means changes its colorimetric, fluorescent, light-scattering, nephelometric, turbidimetric or luminescent state upon contact with the liquid sample.

7. The device of claim 1, in which the first analyte produces an electrochemical signal, and in which the second analyte produces a detectible change in an optical signal, said device containing conducting electrodes to transmit the electrochemical signal, and one or more optical wave guides to transmit the optical signal.

8. The device of claim 1, in which the first analyte produces an electrochemical signal, and in which the second analyte produces a detectible change in an optical signal, said device containing conducting electrodes to transmit the electrochemical signal, and at least one optical wave guide to transmit the optical signal, said optical wave guide consisting of one or more optical fibers.

9. The device of claim 1, in which said first detection zone is an electrochemical reaction zone, and the device contains at least one electrode,
    wherein said electrochemical reaction zone and electrode are mounted on a transparent support;
    said transparent support containing an optical viewing window that enables optical measurements to be performed on said whole blood sample,
    and wherein said second analyte detection zone comprises said optical viewing window.

10. The device of claim 1, in which said first detection zone is an electrochemical reaction zone, and the device contains at least one electrode,
    wherein said electrochemical reaction zone and electrode are mounted on a transparent support;
    said transparent support containing an optical viewing window that enables optical light scattering measurements to be performed on said whole blood sample,
    and wherein said second analyte detection zone comprises said optical viewing window.

11. The device of claim 1, in which said optical signal is a light scattering signal, and said light scattering signal is converted to a clinically meaningful measurement of lipemia.

12. A system for determining the relative concentration of a postprandial lipemia analyte from a single application of a single sample of whole blood; said system comprising a disposable test strip for receiving said sample of whole blood, and an electronic meter;
    said electronic meter having a microprocessor, microprocessor program, visual display, illumination means capable of illuminating said test strip with light with wavelengths greater than about 650 nm, and photodetector means capable of detecting light returned from said test strip;
    said test strip containing optically transmissive materials,
    said optically transmissive materials capable of transmitting light from said light source to said sample of whole blood, and returning scattered light from said sample of whole blood to said photodetector;
    said photodetector producing a scattered light signal that is conveyed to said microprocessor;
    said microprocessor program containing an algorithm that converts said scattered light signal into a measurement of a postprandial lipemia analyte concentration;
    wherein said meter visual display displays said measurement of said postprandial lipemia analyte concentration.

13. The system of claim 12, in which said test strip has materials and geometry are selected to enable the test strip to fully function with a whole blood sample volume under 20 ul.

14. The system of claim 12, in which the meter illuminates the test strip with two or more different wavelengths of light.

15. The system of claim 12, in which said postprandial lipemia analyte is selected from the group consisting of triglycerides, lipoproteins, chylomicrons, and low-density lipoproteins.

16. A method for determining the concentration of two or more analytes in a single sample of whole blood with a volume under 20 ul, comprising the steps of;
   adding said blood sample to a dry reagent diagnostic device in a single application, said dry reagent diagnostic device containing at least two detection zones;
   wherein a first analyte in said sample is determined by a first detection zone, and a second detection zone, physically separated from the first detection zone, determines a second analyte in said sample;
   forming a fluid bridge with the applied blood sample to connect all detection zones on said device;
   said first detection zone and second detection zone having detection zone materials and geometry being selected to allow simultaneous activation of all zones by a single unseparated whole blood drop;
   said detection zone materials and geometry being selected as to return detectable analyte signals in the presence of whole blood;
   and determining the concentration of at least one of said analytes from at least one of said detection zones by a detectable change in an optical signal.

17. The method of claim 16, in which at least one analyte produces an electrochemical signal, and in which at least one analyte produces a detectible change in an optical signal.

18. The method of claim 16, in which the dry reagent diagnostic device contains conducting electrodes to transmit an analyte produced change in an electrochemical signal, and one or more optical wave guides to transmit an analyte produced change in an optical signal.

19. The method of claim 16, in which said detection zone materials and geometry are selected as to generate a detectable sample application signal upon initial contact with whole blood; said detectable sample application signal being capable of triggering an automated detection zone reader which is capable of performing subsequent test timing in an automated manner.

20. The method of claim 16, in which said optical signal is a light scattering signal, and said light scattering signal is converted to a clinically meaningful measurement of lipemia.

* * * * *